(12) United States Patent
Vasan

(10) Patent No.: US 9,993,148 B2
(45) Date of Patent: Jun. 12, 2018

(54) SURGICAL RETRACTOR SYSTEM AND METHOD

(71) Applicant: The Board of Regents of the University of Oklahoma, Norman, OK (US)

(72) Inventor: Nilesh Raman Vasan, Nichols Hills, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 207 days.

(21) Appl. No.: 14/553,787

(22) Filed: Nov. 25, 2014

(65) Prior Publication Data

US 2015/0087918 A1    Mar. 26, 2015

Related U.S. Application Data

(63) Continuation-in-part of application No. PCT/US2013/042700, filed on May 24, 2013.

(60) Provisional application No. 61/651,936, filed on May 25, 2012.

(51) Int. Cl.
| | | |
|---|---|---|
| A61B 1/24 | (2006.01) |
| A61B 1/32 | (2006.01) |
| A61B 13/00 | (2006.01) |
| A61B 17/02 | (2006.01) |
| A61B 17/24 | (2006.01) |
| A61B 90/16 | (2016.01) |
| A61B 90/50 | (2016.01) |

(Continued)

(52) U.S. Cl.
CPC ............... *A61B 1/32* (2013.01); *A61B 1/24* (2013.01); *A61B 13/00* (2013.01); *A61B 17/02* (2013.01); *A61B 17/24* (2013.01); *A61B 90/16* (2016.02); *A61B 90/50* (2016.02); *A61B 1/267* (2013.01); *A61B 2017/00407* (2013.01); *A61B 2017/00477* (2013.01)

(58) Field of Classification Search
CPC ....... A61B 17/0206; A61B 1/24; A61B 17/02; A61B 1/267; A61B 13/00; A61M 16/0495
See application file for complete search history.

(56) References Cited

U.S. PATENT DOCUMENTS

| | | | | |
|---|---|---|---|---|
| 1,388,421 | A | * | 8/1921 | Forgrave ............... A61B 1/24 600/239 |
| 2,697,432 | A | * | 12/1954 | Scinta .................. A61B 1/24 600/239 |

(Continued)

FOREIGN PATENT DOCUMENTS

FR    2 318 614    2/1977

OTHER PUBLICATIONS

European Office Action regarding EP App. No. 13793927.8 dated May 10, 2017, 7 pages.

(Continued)

*Primary Examiner* — Lynnsy Summitt
(74) *Attorney, Agent, or Firm* — Dunlap Codding, P.C.

(57) ABSTRACT

A multiple piece tongue blade is described. The multiple piece tongue blade is provided with a step and a tip. The stem is adapted to be inserted into a handle of a surgical retractor. The tip is adapted to be selectively attached to the stem. The tip is insertable into a mouth of a patient such that the tip applies pressure onto a tongue of the patient.

9 Claims, 17 Drawing Sheets

(51) Int. Cl.
*A61B 1/267* (2006.01)
*A61B 17/00* (2006.01)

(56) References Cited

U.S. PATENT DOCUMENTS

| | | | | |
|---|---|---|---|---|
| 2,947,305 | A | * | 8/1960 | Storz ................. A61B 1/24 600/239 |
| 3,550,584 | A | * | 12/1970 | Ring .................. A61B 1/24 600/205 |
| 3,734,084 | A | | 5/1973 | Ousterhout |
| 3,870,037 | A | * | 3/1975 | Cadariu ............. A61B 1/24 600/185 |
| 4,024,859 | A | | 5/1977 | Slepyan |
| 4,064,873 | A | | 12/1977 | Swenson |
| 5,893,831 | A | | 4/1999 | Koros et al. |
| 6,224,547 | B1 | | 5/2001 | Doyle |
| 6,520,909 | B1 | * | 2/2003 | Rankins ............ A61B 1/00105 600/193 |
| 6,837,883 | B2 | | 1/2005 | Moll et al. |
| 7,806,891 | B2 | | 10/2010 | Nowlin et al. |
| 7,887,483 | B2 | * | 2/2011 | Rosenberg .......... A61B 90/14 600/223 |
| 8,197,402 | B1 | * | 6/2012 | Cedeno .............. A61B 1/24 600/194 |
| 2002/0042620 | A1 | | 4/2002 | Julian et al. |
| 2005/0279355 | A1 | * | 12/2005 | Loubser ........... A61B 1/00103 128/200.26 |
| 2007/0270656 | A1 | | 11/2007 | Bayat |
| 2008/0319270 | A1 | | 12/2008 | Rosenberg |
| 2008/0319370 | A1 | * | 12/2008 | Wolpert ............. A61N 1/0412 604/20 |
| 2009/0204148 | A1 | * | 8/2009 | Lenke ............... A61B 17/02 606/246 |
| 2010/0234857 | A1 | | 9/2010 | Itkowitz et al. |
| 2011/0087265 | A1 | | 4/2011 | Nobis et al. |
| 2012/0031400 | A1 | | 2/2012 | Shimm |

OTHER PUBLICATIONS

PCT International Search Report and Written Opinion for International Application PCT/US2013/042700, dated Aug. 28, 2013.
Leivers, Emery, Improved Davis Mouth Gag, Clinical Notes, New Instruments and Techniques, Sep. 17, 1959.

* cited by examiner

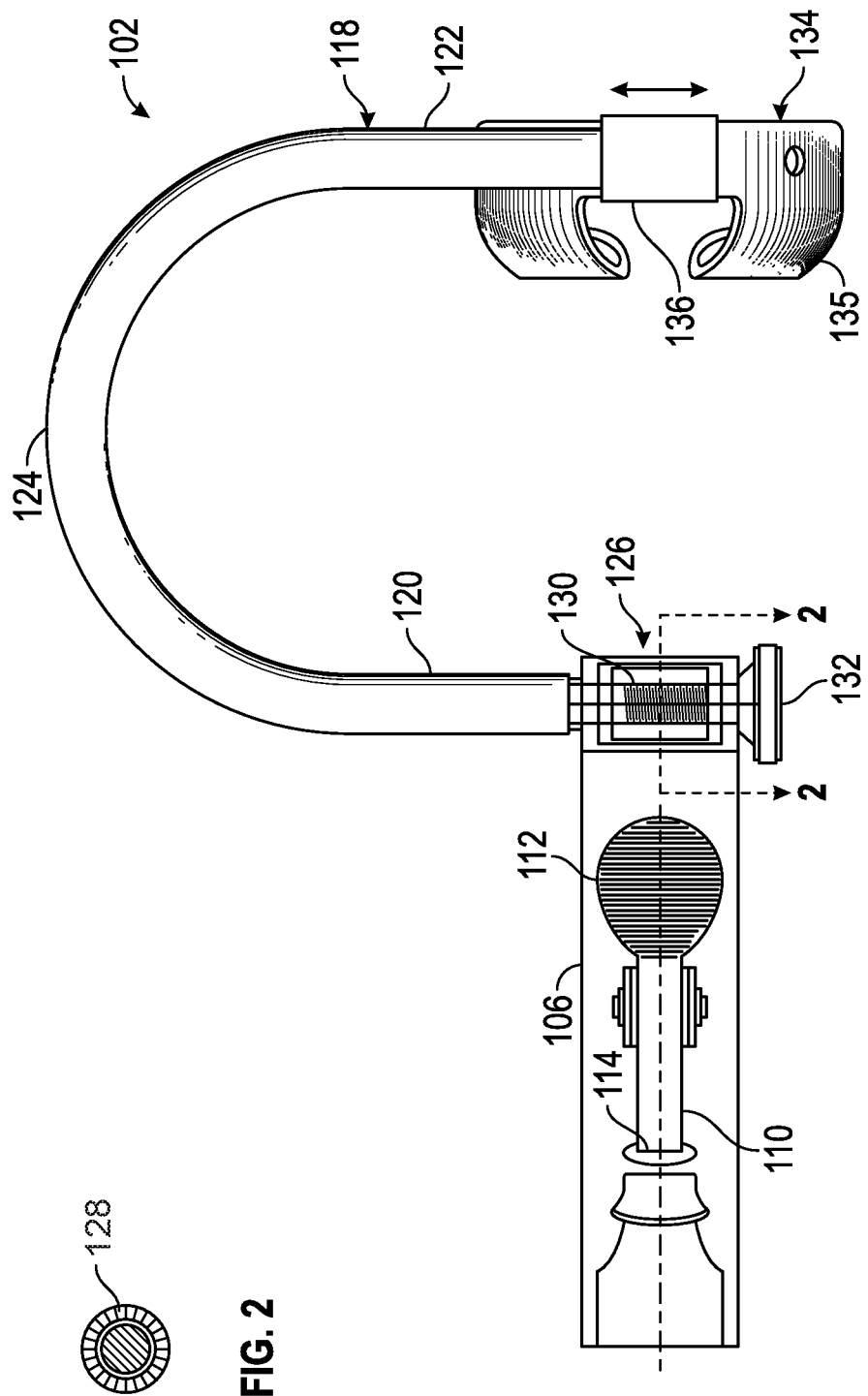

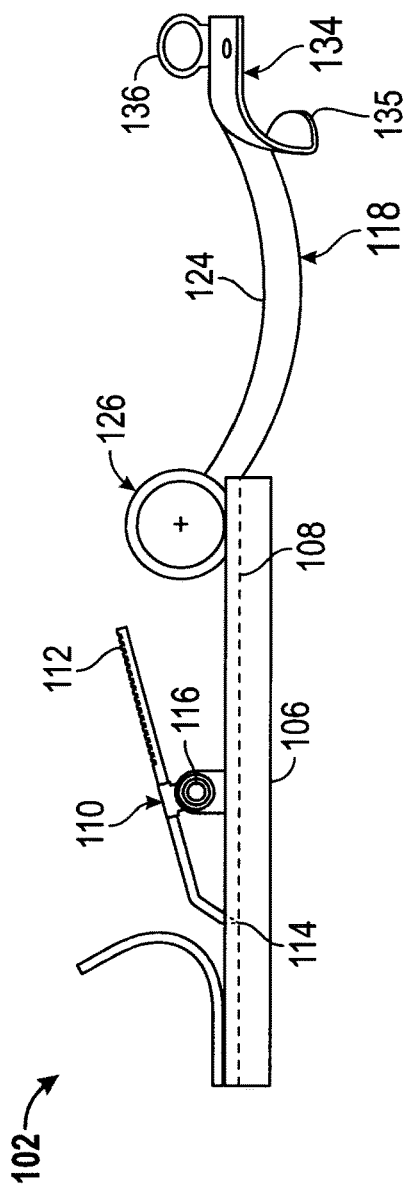
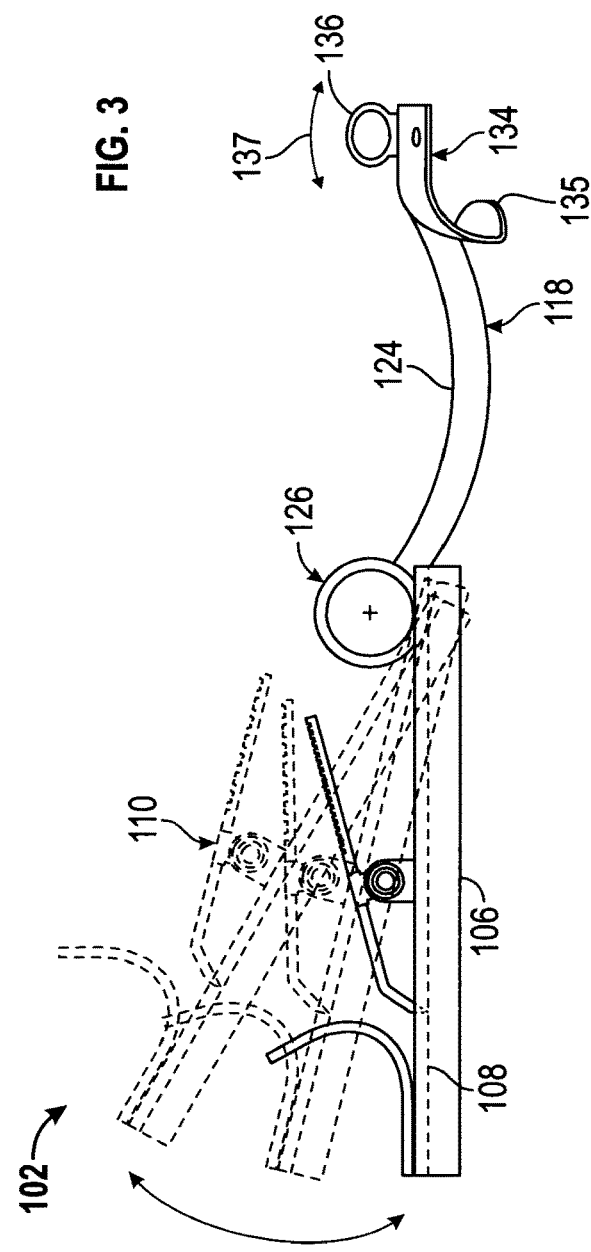
FIG. 3
FIG. 4

SURGICAL RETRACTOR SYSTEM AND METHOD

INCORPORATION BY REFERENCE

The present patent application incorporates by reference and claims priority to the patent application identified by International Application No. PCT/US2013/042700 filed on May 24, 2013, which claims priority to the United States patent application identified by U.S. Ser. No. 61/651,936, filed on May 25, 2012, the entire content of both applications being hereby incorporated herein by reference.

FIELD OF THE INVENTIVE CONCEPTS

The inventive concepts disclosed herein relate generally to surgical retractors, and more particularly, but not by way of limitation to surgical retractor systems and to methods of using thereof.

BACKGROUND

Surgical retractors are known in the prior art and have typically been used to secure a patient's mouth in an open position during a variety of surgical or other medical procedures. Several surgical retractors have found widespread use in the prior art.

The Crowe Davis (or Boyle Davis) surgical retractor (or gag) is a surgical retractor that is primarily used for tonsillectomy and adenoidectomy—very common surgical procedures performed worldwide. A modification to this retractor is the Dingman retractor, which provides surgeons with the additional capability to laterally retract a patient's cheeks for better access to deeper tissues in the mouth and throat. The Dingman surgical retractor, however, is not adapted to allow access deeper into the throat by a surgeon or by a surgical robot.

Recently, the University of Pennsylvania described using the Da Vinci surgical Robot (Intuitive Surgical, Sunnyvale Calif.) to perform surgical procedures within the upper aero-digestive tract called transoral robotic surgery (TORS). The FDA has recently approved of this robotic surgical technique to remove benign and malignant neoplasms from the throat. The University of Pennsylvania group initially described using the standard Crowe Davis gag for surgical procedures involving the tonsils, and later utilized and modified another retractor (FK Retractor, Olympus/Gyrus Germany) to allow access for the robotic arms to other areas in the throat. However, the FK Retractor is expensive, complicated to adjust and use, and has limited adjustability.

Existing surgical retractors are expensive, cumbersome to use, and do not provide the needed adjustability. Further, inserting and removing existing surgical retractors is a complicated procedure which may result in additional trauma to the patient as well as prolonged surgical time. Finally, existing surgical retractors are difficult and slow to remove from the patient's mouth in case of an emergency.

To that end, a need exists for an improved surgical retractor system that is easy to insert and remove and that has interchangeable blades. It is to such a surgical retractor system and method of using thereof that the inventive concepts disclosed herein are directed.

BRIEF DESCRIPTION OF THE DRAWINGS

The following detailed description of various embodiments of the inventive concepts disclosed herein will be better understood when read in conjunction with the appended drawings. For the purposes of illustrating the systems, devices and components of the inventive concepts disclosed herein, exemplary embodiments are shown in the drawings. It should be understood, however, that the inventive concepts disclosed herein are not limited to the precise arrangement, structures, features, embodiments, aspects, and instrumentalities shown, and the arrangements, structures, features, embodiments, aspects, and instrumentalities shown may be used singularly or in combination with other arrangements, structures, features, embodiments, aspects, and instrumentalities. In the drawings:

FIG. 1 is a top view of an exemplary embodiment of a surgical retractor system according to the inventive concepts disclosed herein with the blade removed for clarity.

FIG. 2 is a partial cross-sectional view along lines 2-2 of FIG. 1.

FIG. 3 is a side view of the surgical retractor system of FIG. 1.

FIG. 4 is a side view of the surgical retractor system of FIG. 1 illustrating a lockable hinge that provides adjustability from about 0 degrees to about 360 degrees, while being capable of rigidly and securely locking a bar and a handle at a variety of different angles, which are preferably pre-set.

DETAILED DESCRIPTION OF THE INVENTIVE CONCEPTS

Figure 5:
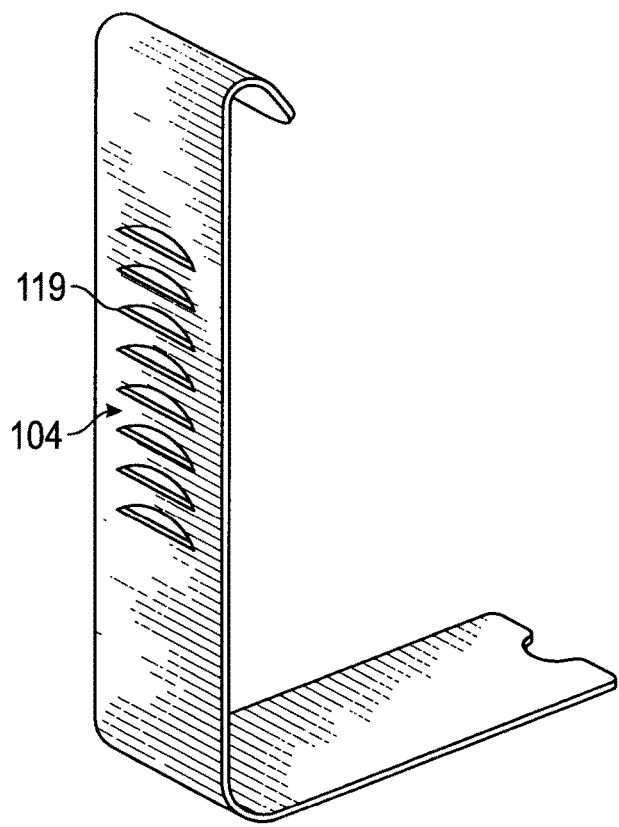
FIG. 5 is a perspective view diagram of a prior art tongue blade.

Before explaining at least one embodiment of the inventive concepts in detail by way of exemplary drawings, experimentation, results, and laboratory procedures, it is to be understood that the inventive concepts are not limited in their application to the details of construction and the arrangement of the components set forth in the following description or illustrated in the drawings, experimentation and/or results. The inventive concepts are capable of other embodiments or of being practiced or carried out in various ways. As such, the language used herein is intended to be given the broadest possible scope and meaning; and the embodiments are meant to be exemplary, and not limiting or exhaustive. Also, it is to be understood that the phraseology and terminology employed herein is for the purpose of description and should not be regarded as limiting.

All patents, published patent applications, and non-patent publications mentioned in the specification are indicative of the level of skill of those skilled in the art to which the inventive concepts disclosed herein pertain. All patents, published patent applications, and non-patent publications referenced in any portion of this application are herein expressly incorporated by reference in their entirety to the same extent as if each individual patent or publication was specifically and individually indicated to be incorporated by reference.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this disclosure, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

The term "about" is used to indicate that a value includes the inherent variation of error for the device, the method being employed to determine the value and/or the variation that exists among study subjects.

Certain embodiments of the inventive concepts will now be discussed with reference to the aforementioned figures, wherein like reference numerals refer to like components. In certain of the figures, not all of the elements may be numerically referenced, where the identity of such an element is clearly evident in reference to said element identified elsewhere in the same or another figure.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein "patient" may refer to a living organism, a dead organism, a synthetic anatomical model, a cadaver, an animal model, a virtual computer model, and combinations thereof, for example.

As used herein, the term "user" may include medical personnel, such as a surgeon, surgical assistant, nurse, a robotic surgical system or arm, veterinary personnel, and combinations thereof, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "combinations thereof" as used herein refers to all permutations and combinations of the listed items preceding the term. For example, "A, B, C, and combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The inventive concepts disclosed herein are directed to a surgical retractor system, and more particularly to an adjustable surgical retractor system having a lockable hinge and replaceable tongue blades, and to methods for using thereof.

Referring now to FIGS. 1-5, in an exemplary embodiment of the inventive concepts disclosed herein, a surgical retractor system 100 comprises a surgical retractor 102 and a tongue blade 104 (FIG. 5).

The surgical retractor 102 may have a handle 106 forming a holder 108 for the tongue blade 104, and including a locking mechanism 110 for slidably adjusting the tongue blade relative to the handle 106. The handle 106 may define a plane, or may be provided with a curved shape to correspond to a curved shape of a stem of a tongue blade as discussed in more detail below to permit adjustment of the stem relative to the handle 106.

The locking mechanism 110 is shown as a ratchet mechanism having a finger rocker 112 and a clevis 114 pivoted by a pin 116, but any conventional locking mechanism that allows for sliding the tongue blade 104 relative to the handle 106 and selectively securing the tongue blade 104 relative to the handle 106 may be implemented with the inventive concepts disclosed herein, for example. The tongue blade 104 may have corresponding ratchet notches 119 adapted to engage the clevis 114 as will be understood by persons of ordinary skill in the art having the benefit of the instant disclosure. Further, the locking mechanism 110 may include one or more devices to avoid inadvertent release during an operation in some embodiments. For example, the locking mechanism 110 may include a pin and lever mechanism, pin lock, retaining pin, and/or other similar device.

The surgical retractor 102 may further have a horizontal U-shaped bar 118 having a first leg 120 and a second leg 122 connected by a curved loop 124. The first leg 120 and the second leg 122 may cooperate to define a plane. The first leg 120 may be attached to the handle 106 via a lockable hinge 126, such that the first leg 120 and the second leg 122 extend in a substantially perpendicular manner relative to the handle 106, and the plane defined by the first leg 120 and the second leg 122 extends relative to the plane defined by the handle 106 at an angle α varying from about 0 degrees to about 360 degrees, for example.

The lockable hinge 126 is desirably lockable at any angle varying between about 0 degrees and about 180 degrees, for example. The lockable hinge 126 may be implemented as any conventional lockable hinge, such as, for example, by a lockable hinge 126 having one or more meshing gear member 128 and a corresponding toothed shaft 130, which may be securely locked or meshed together via a thumb screw 132 to lock the lockable hinge 126. It is to be understood, however, that any suitable lockable hinge 126 may be used with the inventive concepts disclosed herein, provided that such lockable hinge 126 provides adjustability from about 0 degrees to about 360 degrees, while being capable of rigidly and securely locking the bar 118 and the handle 106 at a variety of different angles, which are preferably pre-set. The locking position of the lockable hinge 126 is not limited to any particular position or angle, and the bar 118 and the handle 106 may be positioned in any desired position relative to one another, as will be understood by a person of ordinary skill in the art. The surgical retractor 102 may also include cheek retractors that may be connected to the bar 118. Exemplary cheek retractors are set forth in U.S. Patent Application No. 2008/0319270 titled "Safe Mouth Gag" and are hereby incorporated herein by reference.

Advantageously, a surgeon may adjust the angle between the bar 118 and the handle 106 of the surgical retractor 102 to any desired angle, and then securely lock the lockable hinge 126 of the surgical retractor 102 at that angle. In some exemplary embodiments of the inventive concepts disclosed herein, the surgical retractor 102 may be moved from a first angle surgical angle to a second surgical angle during a surgical procedure. The term "surgical angle" refers to an angle that is desired for use during a surgery, and not intended for insertion or removal of the surgical retractor from the patient. In other exemplary embodiments, the lockable hinge 126 may be used to easily and rapidly remove the surgical retractor system 100 from a patient's mouth during an emergency, desirably without removing the tongue blade 104 from the handle 106.

The second leg 122 may have one or more maxillary brace 134 connected thereto, such that the one or more maxillary brace 134 has a body 135 adapted to engage at least a portion of the patient's maxilla. In one exemplary embodiment, the one or more maxillary brace 134 may be adapted to at least partially engage the patient's maxillary arch, maxillary teeth, maxillary gums, or palate, in order to secure the surgical retractor system 100 into the patient's oral cavity.

In some exemplary embodiments, the one or more maxillary brace 134 may be movable (e.g., rotatable and/or pivotable) relative to the second leg 122, while in other exemplary embodiments, the one or more maxillary brace 134 may be fixed relative to the second leg 122.

In an exemplary embodiment, the one or more maxillary brace 134 may be adjustable and selectively lockable relative to the second leg 122, such that the one or more maxillary brace 134 may be oriented at any desired angle between about 0 and about 360 degrees relative to the second leg 122, and selectively locked in the desired position, such as via a thumb screw (not shown) operated by a user, for example. In another example, the end of the second leg 122 may be hexagonal, square, octagonal, hex key, double hex key, pentalobular, square, triangular, circular, or any other suitable shape, and a correspondingly shaped attachment portion 136 of the maxillary brace 134 may be slid onto the second leg 122 in two or more positions. Further, in some embodiments, the second leg 122 and the one or more maxillary brace 134 may be connected via a lockable hinge (not shown), which may be implemented similarly to the lockable hinge 126, or differently therefrom, for example.

In some exemplary embodiments, the one or more maxillary brace 134 may include a variety of non-slip, or grip-enhancing features, such as rubberized inserts, bumps, grooves, knurls, spikes, and combinations thereof, designed to minimize slipping of the one or more maxillary brace 134 relative to the patient's maxilla. In some embodiments, one or more spikes (not shown) may be implemented with the one or more maxillary brace 134, the one or more spikes designed to engage the soft and/or hard palate tissues of the patient to secure the one or more maxillary brace 134 thereto.

The one or more maxillary brace 134 functions to securely engage the second leg 122 to the patient's maxilla, while at the same time protecting the patient's maxillary tissues, such as palate, gums, and teeth, from damage. In some exemplary embodiments, the one or more maxillary brace 134 may be adapted to engage substantially the entire maxillary arch, and in some embodiments, the one or more maxillary brace 134 may engage portions of the palate, or substantially the entire palate, for example. In other exemplary embodiments, the one or more maxillary brace 134 may engage the patient's maxilla such that the one or more maxillary brace 134 does not come into contact with the patient's maxillary (or upper) teeth, while in other exemplary embodiments the one or more maxillary brace 134 may at least partially contact one or more of the patient's maxillary (or upper) teeth.

In some exemplary embodiments, the one or more maxillary brace 134 may be pivotable relative to the second leg 122, as shown by an arrow 137 which may allow for three-dimensional adjustability of the one or more maxillary brace 134, such that the one or more maxillary brace 134 may be rotated and/or pivoted 360 degrees about the second leg 122 to accommodate varying angles and patient anatomies, and locked in the desired position, such as via a lockable hinge implemented similarly to lockable hinge 126, for example. Further, such adjustability may allow for angular movement of the surgical retractor system 100 as needed during surgical procedures, for example.

In some exemplary embodiments, the surgical retractor 102 according to the inventive concepts disclosed herein may be implemented similarly to the surgical retractor described in U.S. Pat. No. 2,947,305, the entire disclosure of which is hereby expressly incorporated herein by reference, further including the adjustable lockable hinge 126 and/or the adjustable maxillary brace 134 as described above, for example. In other exemplary embodiments of the inventive concepts disclosed herein, a surgical retractor may be implemented similarly to the surgical retractor described in U.S. Pat. No. 4,024,859, the entire disclosure of which is hereby expressly incorporated herein by reference, and may further have an adjustable lockable hinge 126 implemented as described above.

It is to be understood that an adjustable lockable hinge 126 according to the inventive concepts disclosed herein may likewise be implemented with an FK retractor described above in some exemplary embodiments of the inventive concepts disclosed herein.

Further, a surgical retractor 102 according to the inventive concepts disclosed herein may further comprise one or more cheek retractors (not shown), one or more surgical lights (not shown), one or more surgical cameras (not shown), any other suitable attachments usable during a surgical procedure, and various combinations thereof, for example.

The tongue blade 104 is adapted to be slidably received into the handle 106 of the surgical retractor 102, such that the tongue blade 104 may be slidably adjusted relative to the handle 106 and secured at any desired position via the adjustable lockable hinge 126 described above.

It is to be understood that any suitable tongue blade 104 may be used with a surgical retractor system 100 according to the inventive concepts disclosed herein. Further, the tongue blade 104 may have optional features (not shown) such as surgical plume suction channels, channels adapted to receive and retain a surgical tube such as an intubation tube or other surgical tube or cannula, an optical fiber or other camera, surgical lighting, and combinations thereof, for example. For examples of such features, please see U.S. Pat. No. 5,460,626 and U.S. Pat. No. 7,887,483, the entire disclosures of which are hereby expressly incorporated herein by reference. The construction and implementation of the tongue blade 104 are deemed to be within the ordinary skill level in the art, and as such will not be described in detail herein.

Figure 6:
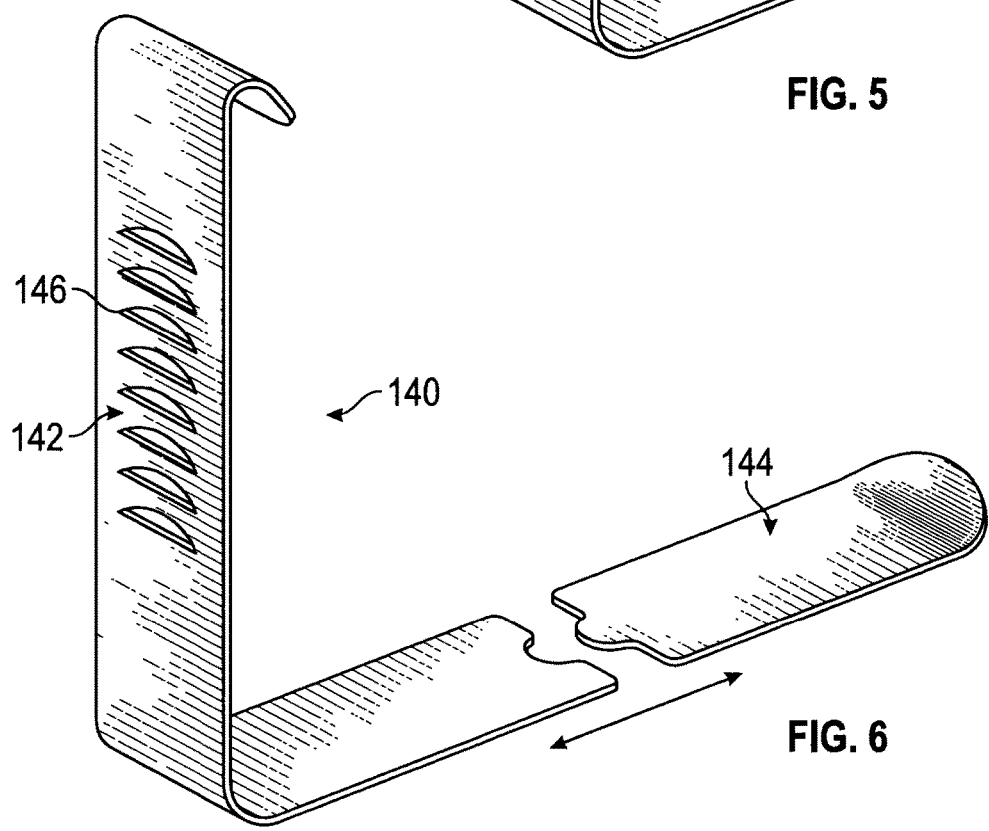
FIG. 6 is a perspective view diagram of an exemplary embodiment of a tongue blade according to the inventive concepts disclosed herein.

Referring now to FIG. 6, a two-piece tongue blade 140 according to the inventive concepts disclosed herein is disclosed. The tongue blade 140 has a stem 142 and a tip 144. The stem 142 may be adapted to be slidably received into the handle 106 of a surgical retractor 102 and may have one or more ratchet grooves 146 formed therein and adapted to engage the locking mechanism 110 of the handle 106. The stem 142 may have a straight portion and a curved portion, may be substantially straight, or may be substantially curved, for example. In some embodiments the stem 142 may have a curvature varying from about 0 degrees to about 180 degrees, for example.

The tip 144 may be adapted to press against a patient's tongue when the tongue blade 140 is inserted into a patient's mouth. The tip 144 and the stem 142 may be attached in a variety of ways as will be described herein below, provided that the stem 142 and the tip 144 are securely attached to one another. In use, the tongue blade 140 may be subjected to significant forces, and the connection between the stem 142 and the tip 144 is desirably able to withstand such forces. The tongue blade 140 may be constructed of any suitable material, such as surgical steel, titanium, polymers, metals, ceramics, and combinations thereof, for example. The tip 144 may have a variety of sizes, depending, for example, on a patient's anatomical features, surgeon preference, surgical procedure, and combinations thereof.

The tongue blade 140 may be formed using any conventional techniques such as machining, forging, pressing, molding, cutting, casting, and combinations thereof, for example.

While it is desirable that no small components are used to connect the stem 142 to the tip 144 to avoid choking or suffocation risks should a small component become detached and fall into the patient's oral cavity or throat, in some exemplary embodiments, a clamp, bracket, thumb screw, hinge, or other mechanisms may be used to connect the tip 144 to the stem 142, such as in veterinary medicine, medical personnel training purposes, autopsy tools, and combinations thereof, for example.

The tongue blade 140 may be used similarly to the tongue blade 104, or differently therefrom, for example.

As will be appreciated by a person of ordinary skill in the art, the two-piece tongue blade 140 provides the ability to implement tips 144 of various sizes, shapes, and configurations to get the desired exposure of oral or throat tissues during surgical procedures. Such blade tips 144 may be patient-specific (or custom), surgeon-specific, or procedure-specific, and combinations thereof, for example. Further, one or more blade tips 144 may be changed or alternated during a single surgical procedure as needed, for example, which may be a different process from that employed with the tongue blade 104.

Figure 7:
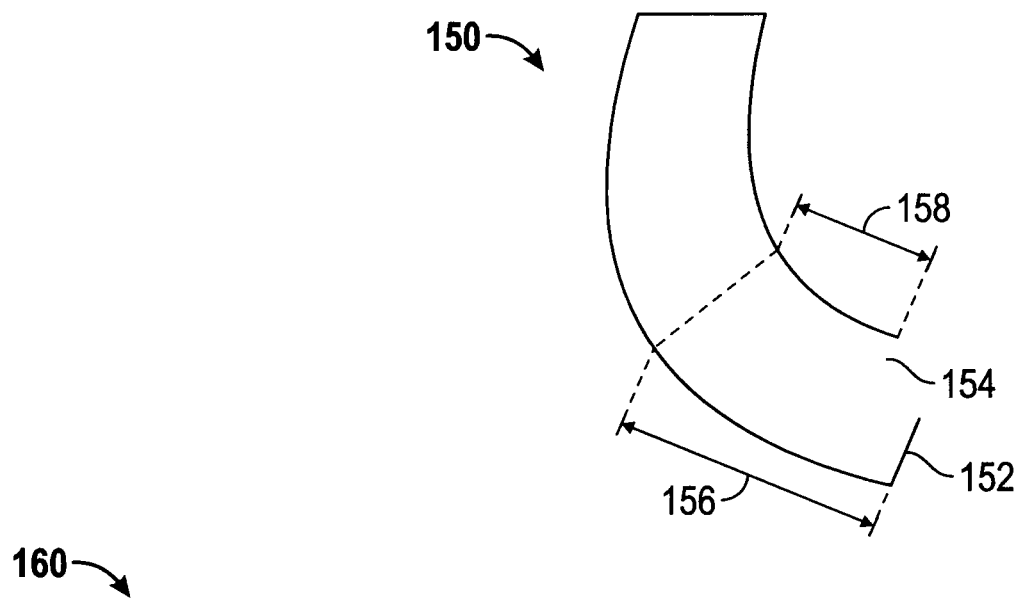
FIG. 7 is a perspective view diagram of an exemplary embodiment of a two-piece tongue blade according to the inventive concepts disclosed herein

Referring now to FIG. 7, in an exemplary embodiment of the inventive concepts disclosed herein, a tongue blade tip 150 is shown as having a first arm 152 and a second arm 154. The tongue blade tip 150 may be adapted to be connected to the stem 142 according to the inventive concepts disclosed herein. The first arm 152 may have a first length 156 and the second arm 154 may have a second length 158. It is to be understood that while the first length 156 is shown as being greater than the second length 158 in FIG. 7, in some exemplary embodiments, the second length 158 may be greater than the first length 156. Further, in some exemplary embodiments the first length 156 and the second length 158 may be substantially equal. In some exemplary embodiments, more than two arms may be implemented, such as three arms, four arms, five arms, and a plurality of arms, which arms may have different, similar, or substantially equal lengths. The tongue blade tip 150 may be implemented as a one-piece blade in some exemplary embodiments of the inventive concepts disclosed herein, and may be implemented similarly to the tongue blade 104, or differently therefrom, for example.

In the exemplary embodiment of the tongue blade tip 150 shown in FIG. 7, the tongue blade tip 150 may be adapted to allow access to one side of the tongue (oral or base). The tongue blade tip 150 may have a left and right sided configuration and allows easy adjustment of the tongue blade tip 150 inserts.

Figure 8:
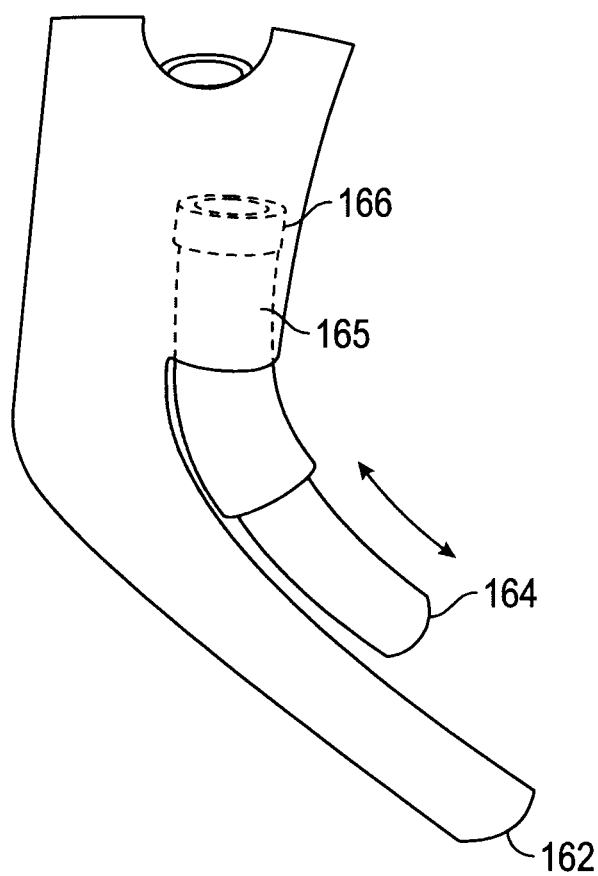
FIG. 8 is a perspective view diagram of the two-piece tongue blade of FIG. 8.

Referring now to FIG. 8, an exemplary embodiment of a tongue blade tip 160 is shown as having a first fixed-length arm 162, and a second adjustable-length arm 164. The second adjustable arm 164 may be slidably received in a recess or sleeve 165 formed in the tongue blade tip 160. The tongue blade tip 160 may also have a handle 166 to assist the user in moving the second adjustable arm 164. The second adjustable arm 164 is maintained within the sleeve 165 by resistance by the tongue. However, a locking mechanism, such as a thumbscrew, may also be provided. It is to be understood however that in some embodiments a tongue blade tip 160 may have two adjustable length arms 164, and the fixed-length arm 162 may be omitted, for example. Further, while the fixed-length arm 162 is shown to the left of the adjustable length arm 164, in some exemplary embodiments the fixed-length arm 162 may be implemented to the right of the adjustable length arm 164. Further, in some exemplary embodiments, two adjustable length arms 164 may be separated or bordered by one or more fixed-length arms 162, while in other exemplary embodiments, one or more fixed-length arms 162 may be separated or bordered by one or more adjustable length arms 164, and combinations thereof, as will be appreciated by persons of ordinary skill in the art presented with the instant disclosure. Further, in some exemplary embodiments of the instant inventive concepts, two, three or more than three fixed-length arms 162 and/or two, three, or more than three adjustable length arms 164 may be implemented with the tongue blade tip 160.

Figure 9:
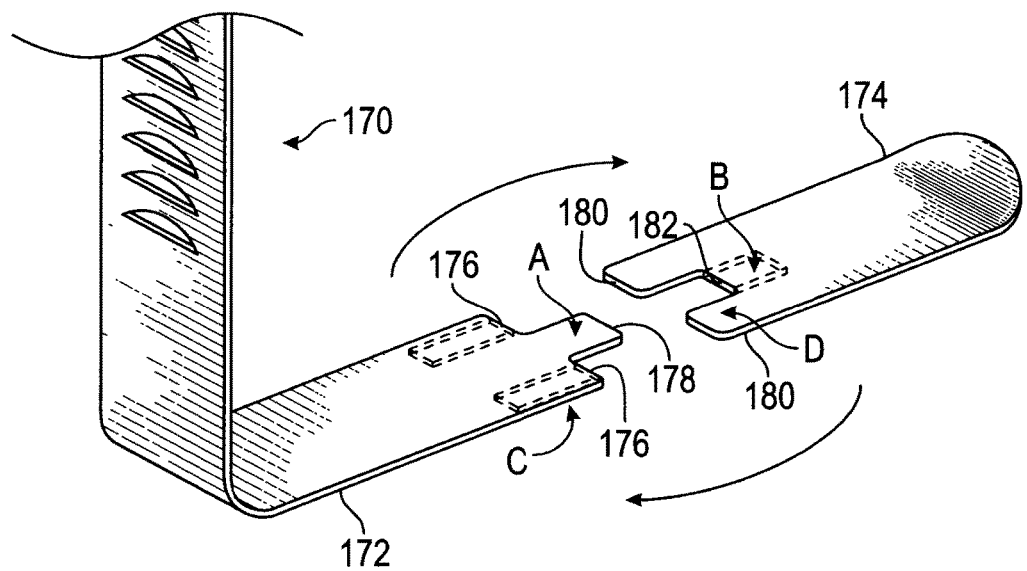
FIG. 9 is a perspective view diagram of an exemplary embodiment of a two-piece tongue blade according to the inventive concepts disclosed herein.
Figure 10:
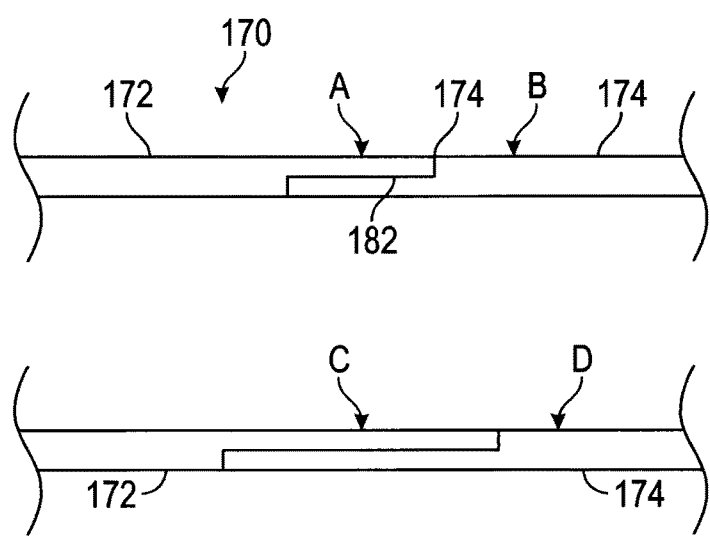
FIG. 10 is a side view diagram of the two-piece tongue blade of FIG. 9.

Referring now to FIGS. 9-10, shown therein is an exemplary embodiment of a tongue blade 170 having a stem 172 and a tip 174. The stem 172 may be adapted to be inserted in a handle 106 of the surgical retractor 102 according to the inventive concepts disclosed herein and may comprise one or more ratchet grooves (not shown) adapted to engage the locking mechanism 110, for example. The stem 172 may have one or more protrusions 176 at an end thereof, and may have one or more notches 178 at the end thereof.

The tip 174 is adapted to be connected to the stem 172 and may comprise one or more protrusions 180 at an end thereof, adapted to fit in the one or more notches 178 defined by the stem 172. The tip 174 may also have one or more notches 182 defined therein, the one or more notches 182 adapted to receive the one or more protrusions 176 of the stem 172. The one or more notches 178 and the one or more notches 182 are desirably positioned on opposing sides of the stem 172 and the tip 174, such that tension is applied to the one or more protrusions 176 and the one or more protrusions 180 when they are inserted into the one or more notches 178 and the one or more notches 182, respectively. This tension may allow the tip 174 to be securely attached to the stem 172 during surgical procedures, for example.

It is to be understood that some exemplary embodiments may implement two or more than two, or may omit one or more of: the one or more protrusions 176, the one or more notches 178, the one or more protrusions 180, and the one or more notches 182.

Figure 11:
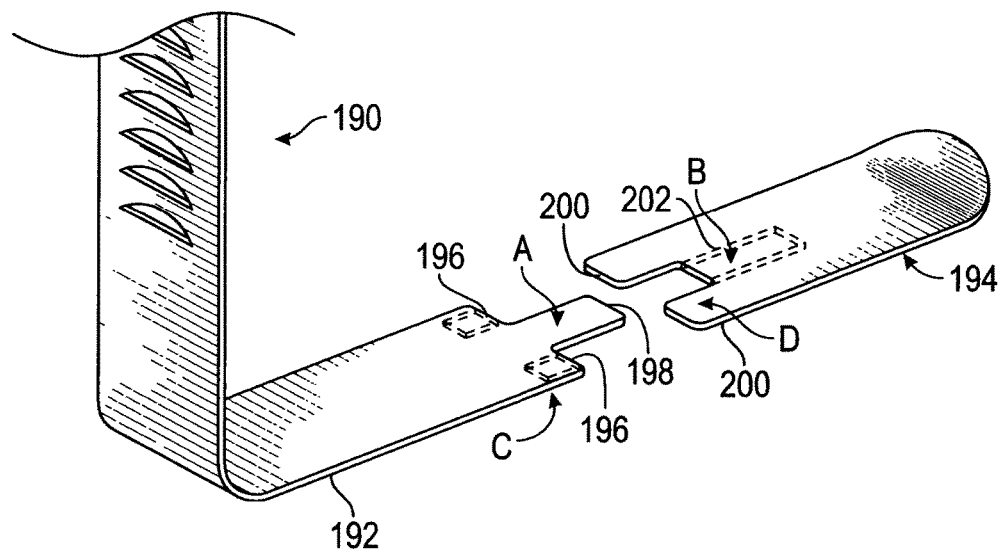
FIG. 11 is a perspective view of an exemplary embodiment of a two-piece tongue blade according to the inventive concepts disclosed herein.
Figure 12:
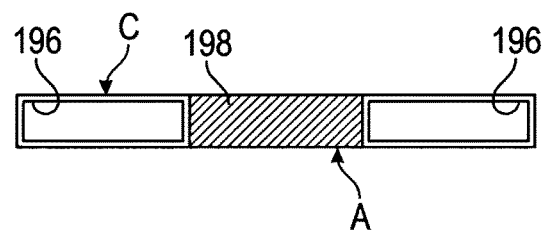
FIG. 12 is an end view of a stem of the two-piece tongue blade of FIG. 11.
Figure 13:
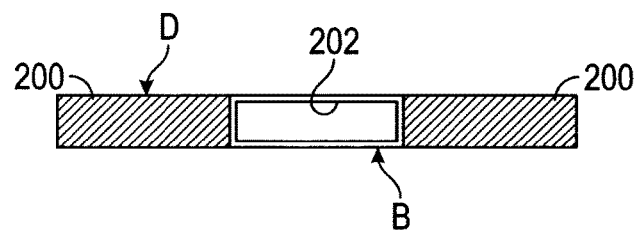
FIG. 13 is an end view of a tip of the two-piece tongue blade of FIG. 11.

Referring now to FIGS. 11-13, an embodiment of a tongue blade 190 is shown as comprising a stem 192 and a tip 194.

The stem 192 is adapted to be inserted in the handle 106 of a surgical retractor 102 according to the inventive concepts disclosed herein or any conventional surgical retractor, and may comprise one or more ratchet grooves (not shown) adapted to engage the locking mechanism 110, for example. The stem 192 may comprise one or more sockets or sleeves 196 and one or more protrusions 198 at an end thereof.

The tip 194 is adapted to be connected to the stem 192 and may comprise one or more protrusions 200 adapted to correspond to and be inserted into the one or more sockets or sleeves 196 of the stem 192, and one or more sockets or sleeves 202 adapted to correspond to and receive the one or more protrusions 198 of the stem 192, for example. The tip 194 may be attached to the stem 192 by inserting the one or more protrusions 198 into the one or more sockets or sleeves 202 and by inserting the one or more protrusions 200 into the one or more sockets or sleeves 196, for example.

It is to be understood that in some exemplary embodiments of the inventive concepts disclosed herein, two or more than two sockets or sleeves 196 may be implemented. Further, in some exemplary embodiments two or more than two protrusions 198 may be implemented, while in other exemplary embodiments the protrusions 198 may be omitted. In some exemplary embodiments, two or more than two protrusions 200 may be implemented, while in other exemplary embodiments two or more than two sockets or sleeves 202 may be implemented. Further, some exemplary embodiments may omit one or more of: the one or more sockets or sleeves 196, the one or more protrusions 198, the one or more sockets or sleeves 202, and the one or more protrusions 200.

The tongue blade 190 may be implemented similarly to the tongue blade 104, or differently therefrom, for example.

Referring now to FIGS. 14-18, in some cases, Obstructive Sleep Apnea (OSA) may be caused by prominent tissue located at the base of the patient's tongue, which prominent tissue may obstruct the airways of the patient. Such prominent tissue may be surgically removed to treat OSA in some patients. The surgical removal of the prominent tissue at the base of the tongue may be performed by a surgeon or may be achieved with a surgical robot, and combinations thereof, for example.

Figure 14:
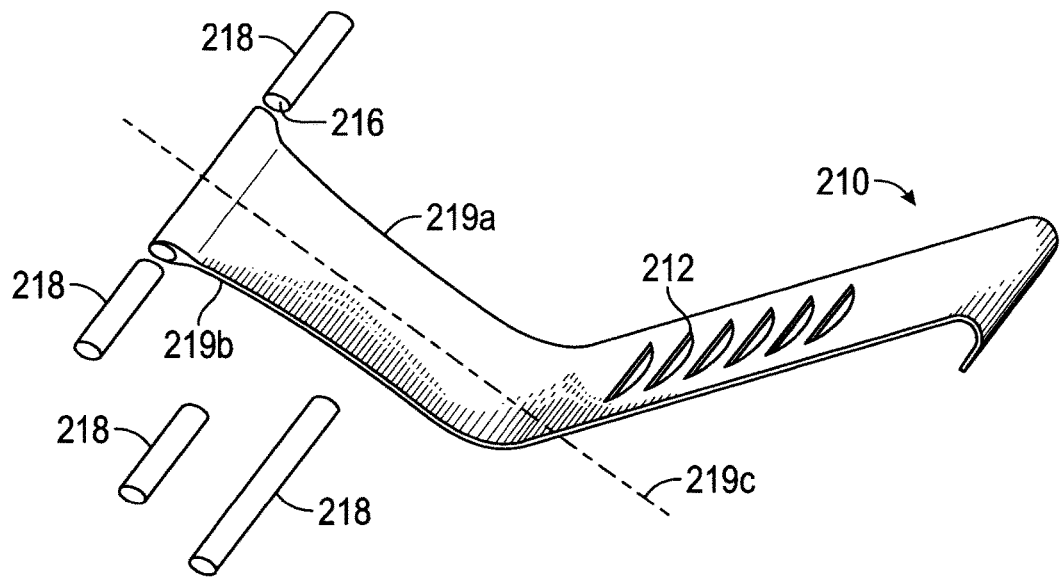
FIG. 14 is a perspective view of an adjustable tongue blade according to the inventive concepts disclosed herein.

An exemplary embodiment of a tongue blade 210 (FIG. 14) may be used with a surgical retractor system 100 according to the inventive concepts disclosed herein to isolate and remove the prominent tissue at the base of the tongue. The tongue blade 210 is designed so that it has a stem 212 adapted to be slidably inserted into a surgical retractor handle 106 and a tip 214 which includes a holder 216 adapted to receive and selectively retain a pin 218 therein. The pin 218 may have a cylindrical, octagonal, or hexagonal shape, for example. In some exemplary embodiments, the pin 218 may have a first portion with a first shape, and a second portion with a second shape, or more than two portions with various shapes as will be understood by persons of ordinary skill in the art having the benefit of the instant disclosure. It is to be understood that while a pin 218 and a holder 216 are shown in FIG. 14, the inventive concepts disclosed herein may be implemented with two or more than two pins 218 and/or holders 216, for example.

The tip 214 may have a first side 219a and a second side 219b. In one embodiment, the pin 218 extends beyond the first side 219a, and/or the second side 219b. For example, as shown in FIG. 14, the pin 218 may extend perpendicular to a major axis 219c of the tip 214.

Figure 18:
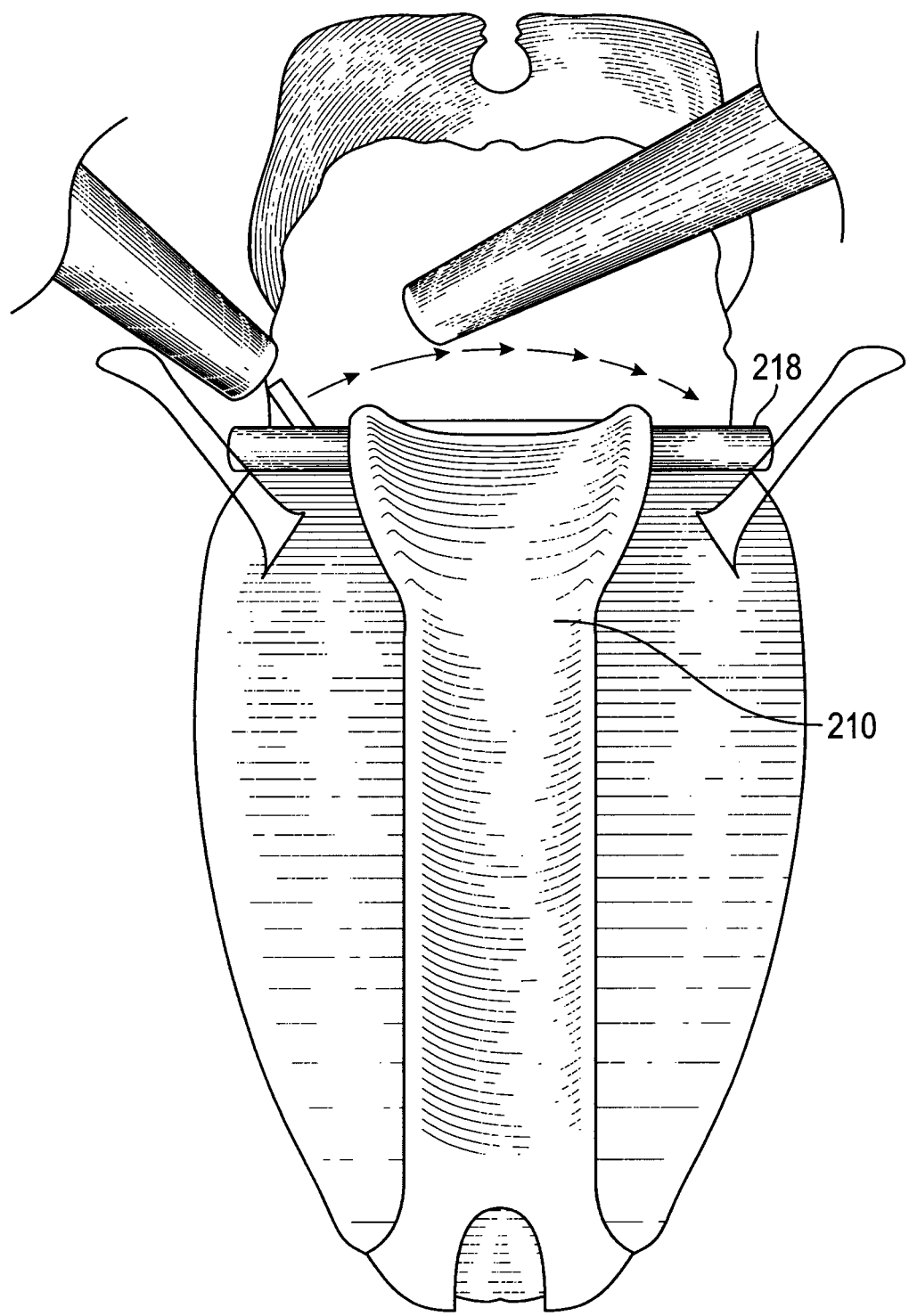
FIG. 18 is a diagram of a base of tongue tissue removal using a surgical retractor system according to the inventive concepts disclosed herein.

The tip 214 of the tongue blade 210 may sit against the part of the back of the tongue where the tissue would be dissected. Varying the sizes, length, thickness, and shapes of the pin 218 would be used to accommodate varying tongue widths, for example. The pin 218 may function to press up, roll up, push up, or otherwise isolate the prominent tissue at the back of the tongue. The prominent tissue pressed up by the pin 218 may then be surgically removed, such as via a laser, cold steel, electocautery, harmonic cautery, coblation or robotic shears, for example (FIG. 18).

The detachable tip 214 may be selectively connected and disconnected to the main portion or stem 212 of the tongue blade 210. The detachable tip 214 may be adapted to be oriented up or down and may be oriented at a variety of angles relative to the stem 212, such as from about 0 degrees to about 360 degrees, for example. This would allow a surgeon to connect a variety of different blade tips 214 of various sizes to the stem 212 to get the best exposure for each surgical procedure and/or patient.

Figure 15:
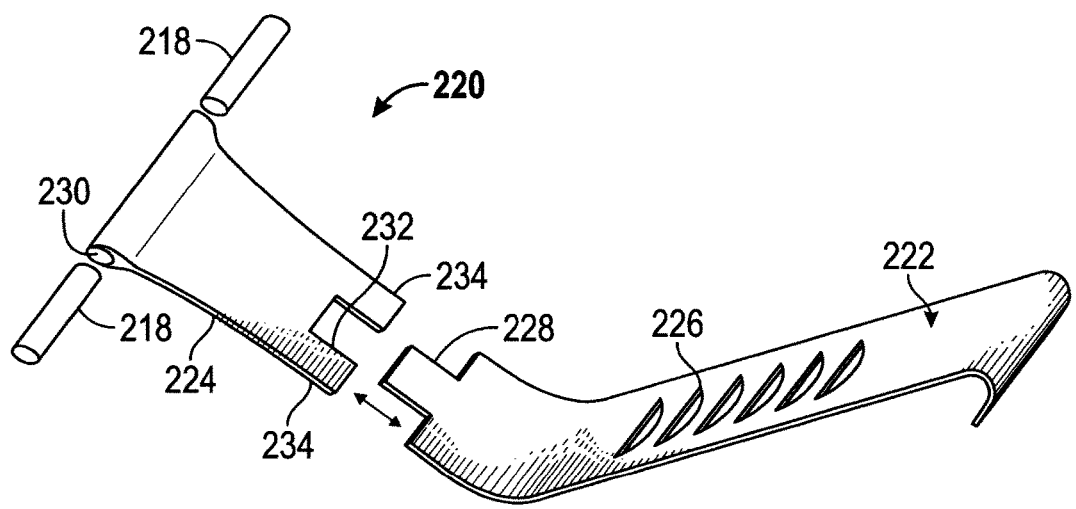
FIG. 15 is a perspective view of an exemplary embodiment of a tongue blade according to the inventive concepts disclosed herein.

Referring now to FIG. 15, an exemplary embodiment of a tongue blade 220 may have a two-piece design and may include a stem 222 and a tip 224. The stem 222 may be adapted to be slidably received in the handle 106 of the surgical retractor 102 according to the inventive concepts disclosed herein, and may be implemented similarly to the stem 172 (FIG. 9) described above. The stem 222 may be connected to the tip 224 in any suitable manner, such as one or more grooves 226 adapted to engage the locking mechanism 110, for example. The stem 222 may further have one or more protrusions 228 which may be implemented similarly to the one or more protrusion 176 described above.

The tip 224 has a holder 230 adapted to hold one or more surgical pin 218 therein and may be implemented similarly to the stem 212 of the tongue blade 210, or differently therefrom, for example. The tip 224 may further have one or more notches 232 and one or more protrusions 234 at an end thereof, the one or more notches 232 may be adapted to receive the one or more protrusion 228 therein, and the one or more protrusions 234 may be adapted to engage corresponding notches (not shown), grooves (not shown), or recesses (not shown) in the stem 222, such that the tip 224 is securely attached to the stem 222, for example.

Figure 16:
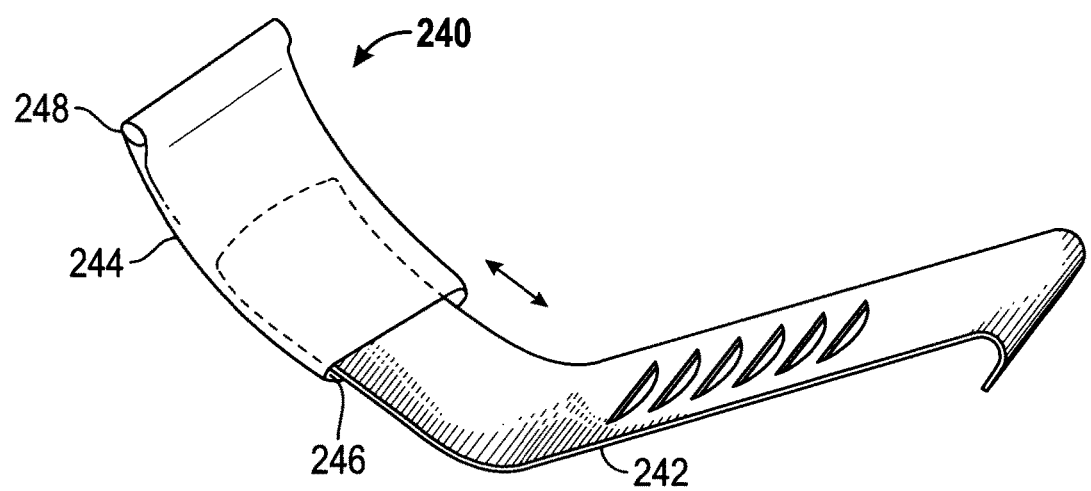
FIG. 16 is a perspective view of an exemplary embodiment of a tongue blade according to the inventive concepts disclosed herein.
Figure 17:
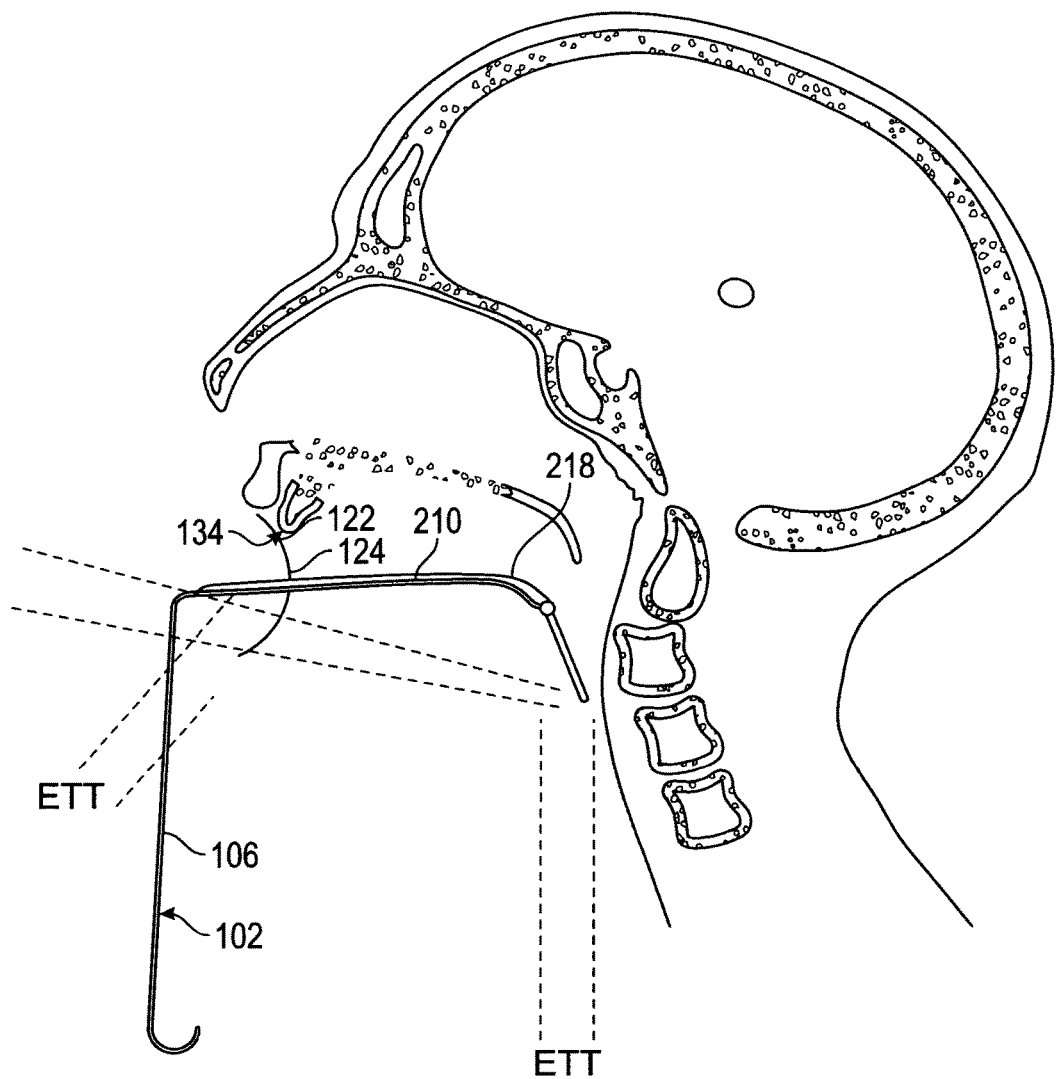
FIG. 17 is a diagram of a retractor system positioned in a patient's mouth according to the inventive concepts disclosed herein.

An exemplary embodiment of a tongue blade 240 shown in FIG. 16 may be adjustable to allow manipulation of the tongue blade 240 while the tongue blade 240 is inserted into a patient's oral cavity. The tongue blade 240 may be implemented similarly to the tongue blade 104 described above or differently therefrom, and may have a stem 242 and a tip 244, defining a sleeve 246. The stem 242 may be adapted to be slidably received inside the sleeve 246. In the exemplary embodiment shown in FIG. 16 the tongue blade 240 may have a mild curvature, such as between about 0 degrees and about 30 degrees. A blade sliding mechanism may have small attachments on its side (not shown) to allow sliding action of the tongue blade 240. The tongue blade 240 may also be held in place by the fact that, in use, the tongue blade 240 is pressed against the tongue which causes a corresponding force against the tip 244 and the stem 242. In other words, pressing the tip 244 and the stem 242 can be designed such that placing a force against the tip 244 causes the tip 244 and the stem 242 to remain together. However, it should be understood that the tip 244 and the stem 242 can be designed in other ways to connect the tip 244 to the stem 242. The tongue blade 240 may further have a holder 248 adapted to hold a surgical pin 218 therein.

As will be understood by persons of ordinary skill in the art, several connecting mechanisms may be implemented with the inventive concepts disclosed herein, to ensure secure attachment of the tip to the main portion of the blade, as long as such connecting mechanisms are reliable, strong, and durable. For example, as described above prongs or segments of the opposing blade tip may insert into a space or socket of the stem of the blade. This may result in a more secure connection between the stem and the tip, but may also require slightly increasing the width of the blade to accommodate the sockets.

The particular type of connector between the tip and the stem of the blade used, the connector desirably is able to withstand the large amount of strain that is typically applied to a tongue blade, as will be recognized by persons of ordinary skill in the art. The blade tip may be of any desired shape, size, width, curvature, length, and configuration.

Figure 22:
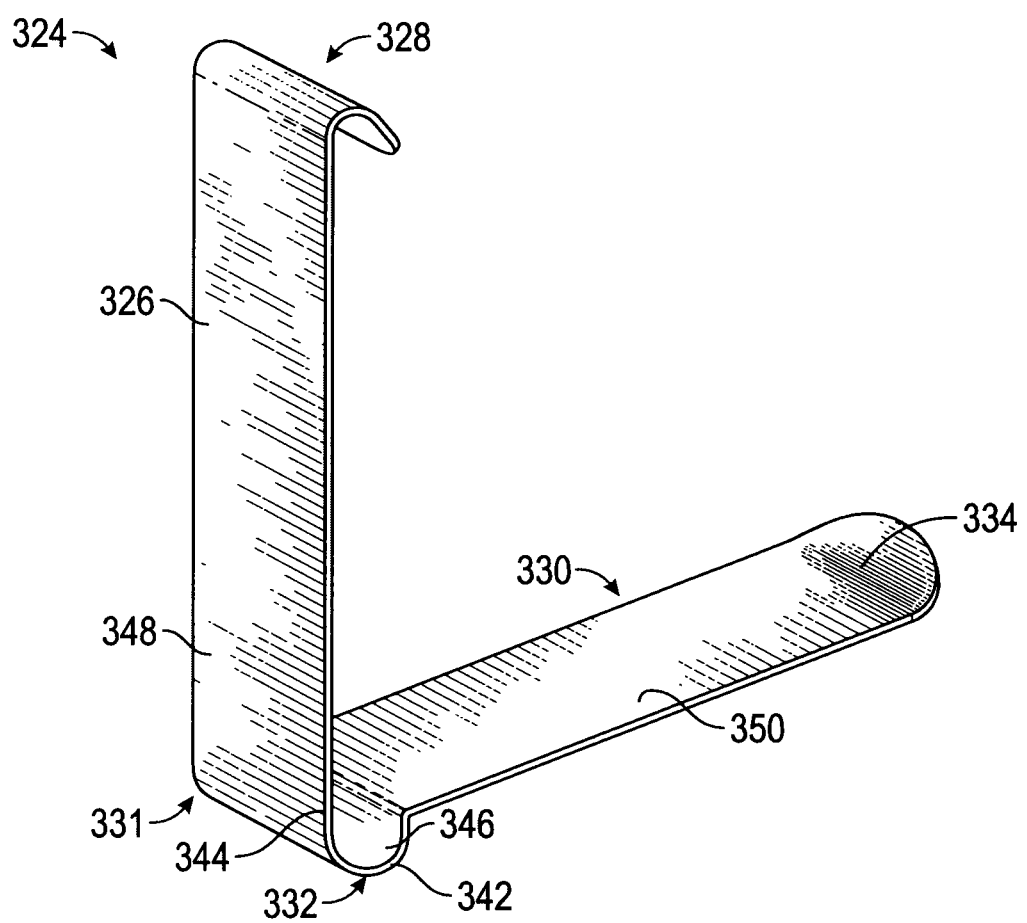
FIG. 22 is a perspective view of an exemplary embodiment of a tongue blade according to inventive concepts disclosed herein.
Figure 23:
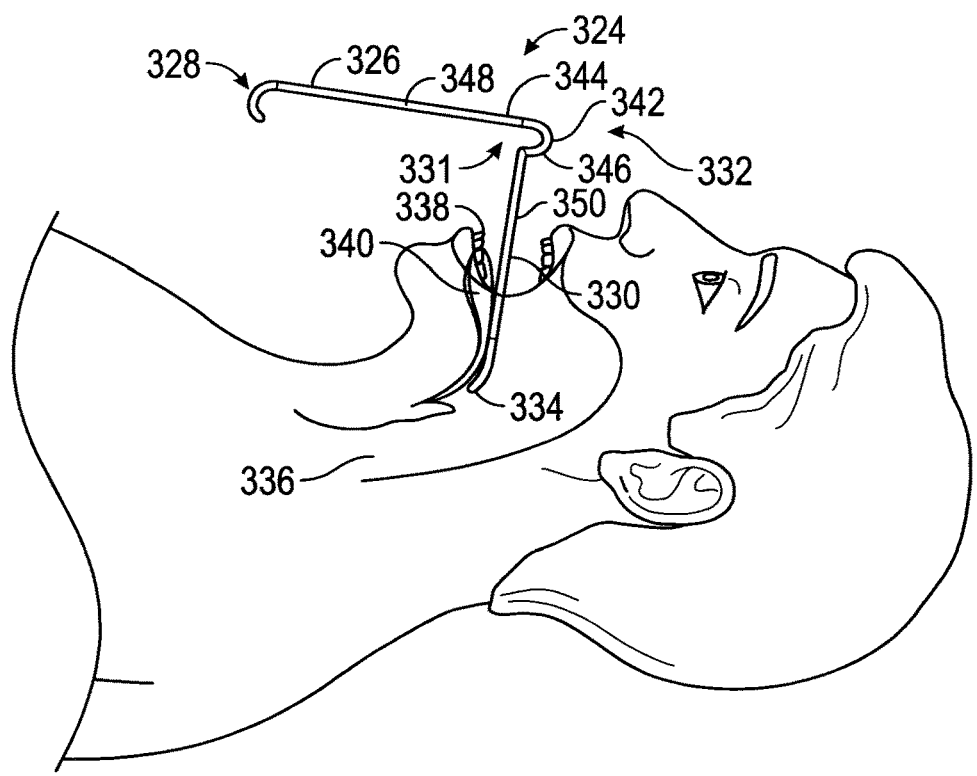
FIG. 23 is a side view of the tongue blade of FIG. 22 in relation to mandibular teeth of a patient.
Figure 24:
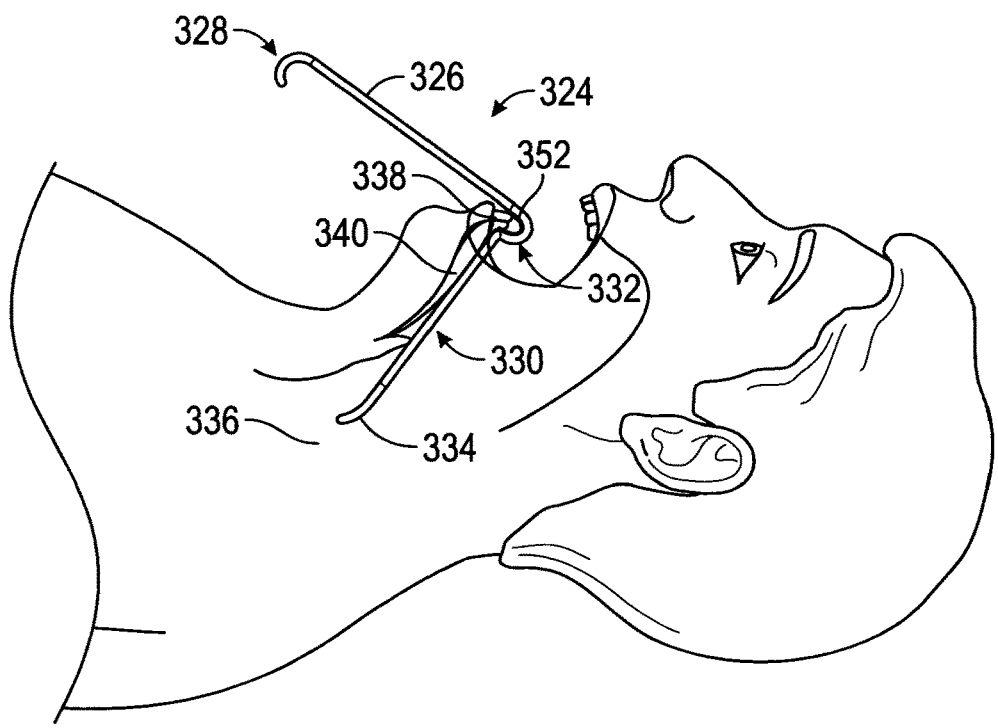
FIG. 24 is a side view of the tongue blade of FIG. 23 having mandibular teeth of a patient received within a U-shaped groove of the tongue blade.

Referring now to FIGS. 22-24, an exemplary embodiment of a substantially L-shaped tongue blade 324 that may include a stem 326 having a proximal portion 328 and a distal portion 330 that may be positioned normal to each other. The proximal portion 328 and the distal portion 330 can be constructed as separate items that are subsequently connected together, or be integrally formed and connected via a connecting portion 331 in the shape of a curvature or bend provided at an intersection of the proximal portion 328 and the distal portion 330. The connecting portion 331 may be provided between the proximal portion 328 and the distal portion 330. In some embodiments, the connecting portion 331 may support the proximal portion 328 and the distal portion 330 at an angle of approximately 90 degrees, for example. The stem 326 may include a teeth receiving section 332. The stem 326 may be adapted to be slidably received in the handle 106 of the surgical retractor 102 illustrated in FIG. 1 according to the inventive concepts disclosed herein, and may be implemented similarly to the stems 142, 172, 192, 212 described herein, for example.

In some embodiments, a tip 334 may be permanently connected to or an integral part of the distal portion 330 of the stem 326, or removably connected to the stem 326 in any suitable manner, such as a locking mechanism (e.g., locking mechanism 110) as described above, for example. The tip 334 may be shaped and adapted to be used for retracting a tongue of a patient to provide access to a throat 336 of the patient. Further, the stem 326 may include one or more protrusions on the proximal portion 328 which may be implemented similarly to the one or more protrusions 176, 228 described above, for example. The tip 334 may be of any desired shape, size, width, curvature, length and configuration that may be inserted into a patient's mouth and used to retract the patient's tongue to provide access to the patient's throat 336.

Referring to FIGS. 23-24, the teeth receiving section 332 of the stem 326 may be in the form of a U-shaped groove that is shaped to receive, negotiate around or avoid mandibular teeth 338 of a patient and thereby increase access to the throat 336. The U-shaped groove has an opening positioned to receive at least a portion of a patient's mandibular teeth 338 when the tip 334 is inserted into the mouth of the patient. For example, the opening may face the proximal portion 328. By negotiating around mandibular teeth 338 of a patient, the surgical retractor 102, illustrated in FIG. 1, may have increased access to the throat 336. As illustrated in FIG. 24, in some embodiments, with the one or more mandibular teeth 338 received within the U-shaped groove of the teeth receiving section 332, the tongue 340 of the patient may be moved and/or retracted further. It should be noted that the teeth receiving section 332 may be implemented into any of the embodiments of tongue blades described herein. Although a U-shaped groove is illustrated, any shape capable of receiving mandibular teeth 338 may be used.

The teeth receiving section 332 may include a first end 342 connecting a first side 344 of the teeth receiving section 332 to a second side 346 of the teeth receiving section 332. The first side 344 and the second side 346 may extend away from the distal portion 330 in a normal direction. The first side 344 and the second side 346 may also extend in a direction generally parallel with a longitudinal axis of the proximal portion 328. The first side 344 may be connected to a first portion 348 of the proximal portion 328 of the stem 326 and the second side 346 may be connected to a second portion 350 of the distal portion 330 of the stem 326. In this example, the teeth receiving section 332 is a part of the connection portion 331, although it should be understood that the teeth receiving section 332 could be part of the distal portion 330. The teeth receiving section 332 may be of any size, width, curvature, and configuration such that the one or more mandibular teeth 338 are capable of being received within the teeth receiving section 332.

In some embodiments, the tongue blade 324 may include one or more layers of padding 352 positioned within the teeth receiving section 332. For example, in some embodiments, the a layer of padding 352 formed of silastic, or other similar material may be positioned within the teeth receiving section 332 to be between the teeth receiving section 332 and the patient's mandibular teeth 338 to protect the patient's mandibular teeth 338 from contacting the teeth receiving section 332. In some embodiments, one or more layers of padding 352 may extend the length of the teeth receiving section 332 from the first side 344 to the second side 346. Alternatively, one or more layers of padding 352 may extend a portion of the length of the teeth receiving section 332. In some embodiments, one or more layers of padding 352 may be capable of being detachably removed.

Figure 25:
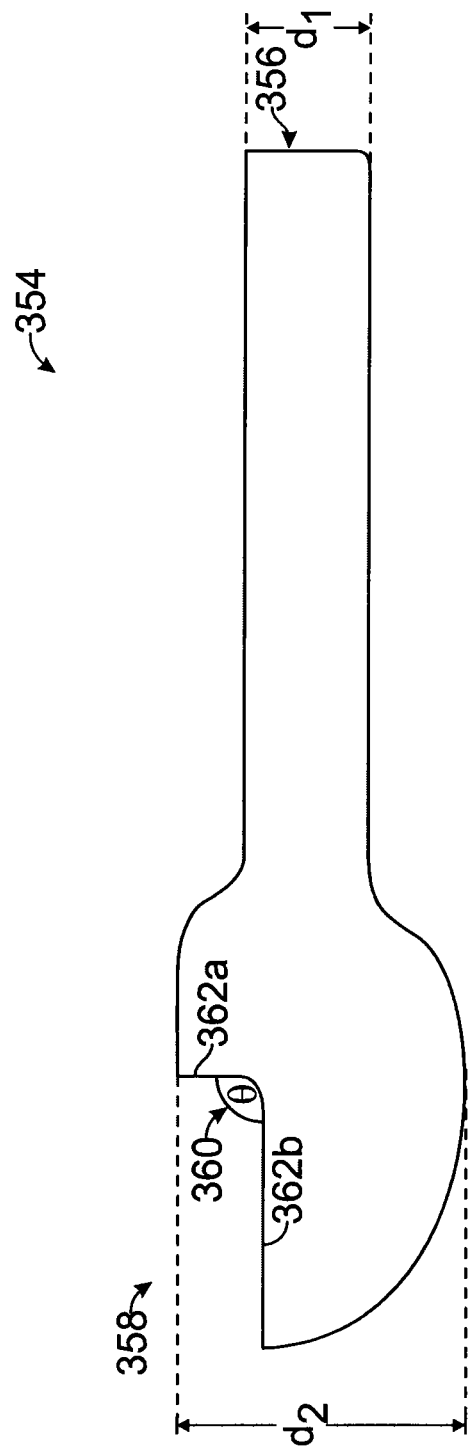
FIG. 25 is a top down view of an exemplary tip for use in a tongue blade according to inventive concepts disclosed herein.

Referring now to FIG. 25, illustrated therein is an exemplary tip 354 for use in any tongue blade disclosed herein such as tongue blades 104, 140, 170, 190, 210, 220, 240, and 324, for example. The tip 354 has a proximal end 356 and a distal end 358, the proximal end 356 capable of attaching to a stem as described in further detail herein. In some embodiments, one or more protrusions, as described in detail herein, may be positioned on the tip 354.

In some embodiments, the proximal end 356 may have a smaller diameter $d_1$ as compared to the diameter $d_2$ of the distal end 358 as illustrated in FIG. 25. In some embodiments, the diameter $d_1$ may be similar to the diameter $d_2$ or larger than diameter $d_2$.

The distal end 358 of the tip 354 may include a notch 360. The notch 360 may include one or more sides 362 forming an indentation within the distal end 358 of the tip 354. For example, in FIG. 25, a first side 362a and a second side 362b form an angular indentation Θ within the distal end 358 of the tip 354. Although the angular indentation formed in the distal end 358 of the tip 354 is illustrated as about 90 degrees, it should be noted that any angle between 60-120 degrees may be used.

Figure 19:
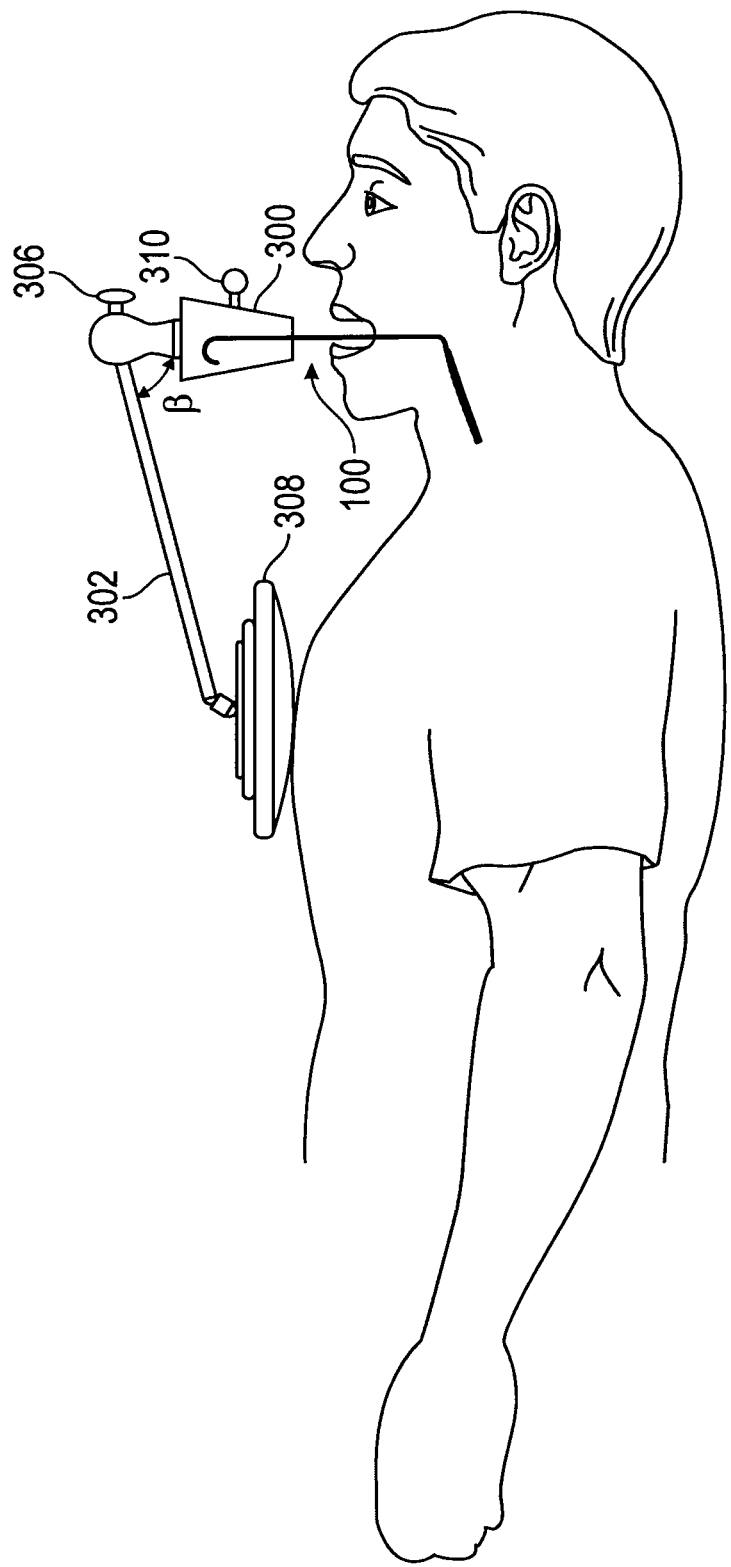
FIG. 19 is a perspective view of an exemplary embodiment of a support brace according to the inventive concepts disclosed herein.
Figure 20:
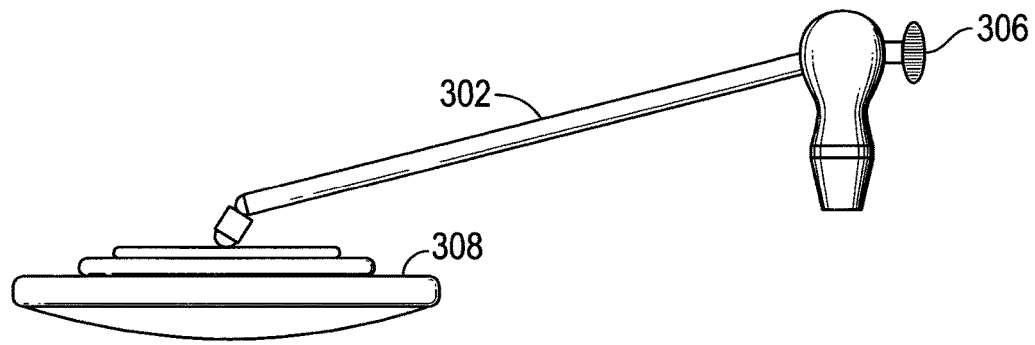
FIG. 20 is a perspective view diagram of the support brace of FIG. 20.
Figure 21:
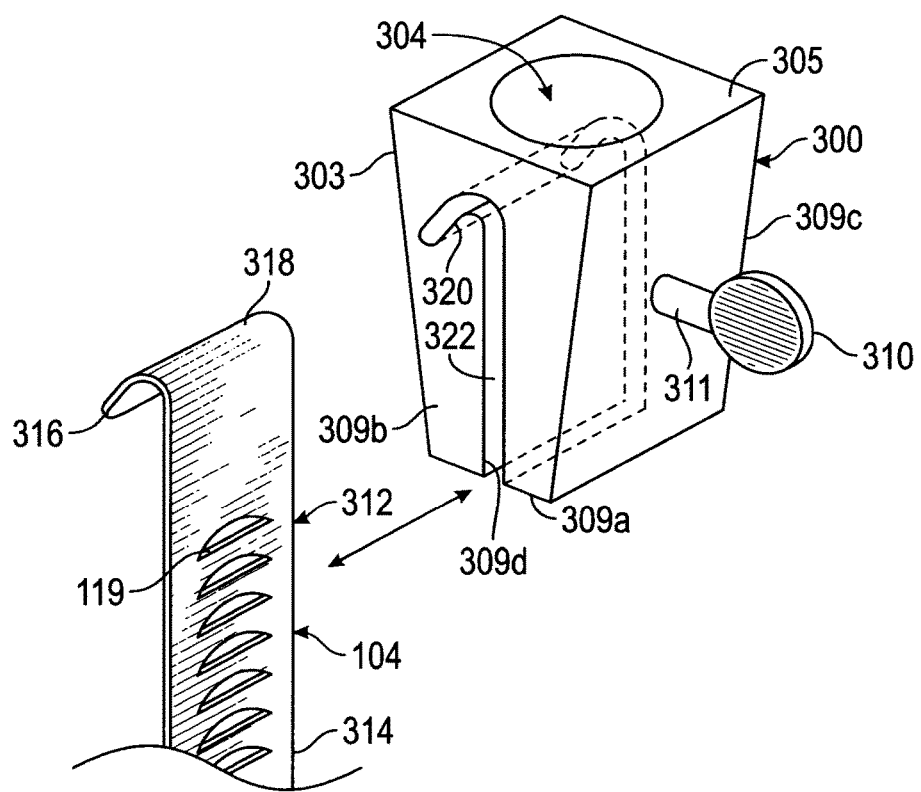
FIG. 21 is a diagram of an exemplary embodiment of a support brace according to the inventive concepts disclosed herein.

Referring now to FIGS. 19-21, a support bracket 300 for a surgical retractor system 100 according to the inventive concepts disclosed herein is shown. In some implementations, surgical retractor systems 100 may require additional support that may be provided by a support brace 302. However, there are currently no similar supporting mechanisms for the end of a Crowe-Davis or Dingman retractors or for surgical retractors according to the inventive concepts disclosed herein.

The support bracket 300 has a body 303 having a first slot 304 on an upper end 305 thereof. The support brace 302 of the surgical retractor system 100 connects to the body 303 by insertion of the support brace 302 into the slot 304 on the upper end of the support bracket 300. The connection between the support brace 302 and the body 303 of the support bracket 300 may be secured with a thumbscrew 306 or any other locking and/or securing mechanism, and the support brace 302 may be supported either on the patient, or on a supporting surface such as a surgical table 308, for example.

The body 303 of the support bracket 300 according to the inventive concepts disclosed herein may fit into the same standard slot as a laryngoscope. The body 303 of the support bracket 300 may be adapted to fit in a standard slot of the support brace 302. The body 303 may have a lower end 309a, a first side 309b extending between the upper end 305 and the lower end 309a, and a second side 309c extending between the upper end 305 and the lower end 309a. The body 303 may also be provided with a slot 309d extending through the lower end 309a and intersecting the first side 309b. The slot 309d may be designed such that the end of the tongue blade 104 of the surgical retractor 102 may be slidably inserted into the support bracket 300 and secured therein by a thumbscrew 310, for example which has a member 311 selectively projecting into the slot 309d. The tongue blade 104 has a stem 312 designed to be inserted into the handle 106 of the surgical retractor 102. More particularly, as shown in FIG. 21, the stem 312 is provided with an adjustment portion 314 that includes the ratchet notches 119 adapted to engage the clevis 114. The stem 312 is also provided with an end 316 and an arc-shaped portion 318 between the adjustment portion 314 and the end 316. In one embodiment, the slot 309d is sized and shaped to receive at least a portion of the adjustment portion 314 and the entire arc-shaped portion 318 of the stem 312. In this embodiment, the slot 309d is provided with a first portion 320 having an arc-shape corresponding to the arc-shaped portion 318, and a second portion 322 having a shape corresponding to the shape of the adjustment portion 314, which as discussed above can be a linear shape or an arc-shape. The support bracket 300 may be constructed of any suitable material with sufficient strength, such as metals, steel, titanium, polymers, plastics, and combinations thereof, for example. In some exemplary embodiments, the support bracket 300 may be constructed of a solid metal, such as titanium or surgical steel to ensure sufficient strength and durability.

The support brace 302 may be a conventional laryngoscope support brace as will be understood by a person of ordinary skill in the art having the benefit of the instant disclosure. The support brace 302 is desirably sturdy and allows increased elevation of the surgical retractor system 100 and provides rigid support for the surgical retractor system 100. The support brace 302 and support bracket 300 combination may be used with any conventional surgical retractor system as well, and may be utilized in a variety of surgical procedures, for example.

In the exemplary embodiment shown in FIG. 19, the support brace 302 is used such that the surgical retractor system 100 is supported at an angle β relative to the support brace 302, which angle β may vary between about 0 and about 180 degrees. Desirably, the surgical retractor 102 is supported such that the surgical retractor 102 is oriented substantially vertically relative to the patient, which allows increased access inside the patient's oral cavity by surgeons or robotic arms, for example. It is to be understood however, that the surgical retractor 102 may be supported at any angle relative to the patient, such as an angle varying from about 0 to about 180 degrees, for example.

Figure 26:
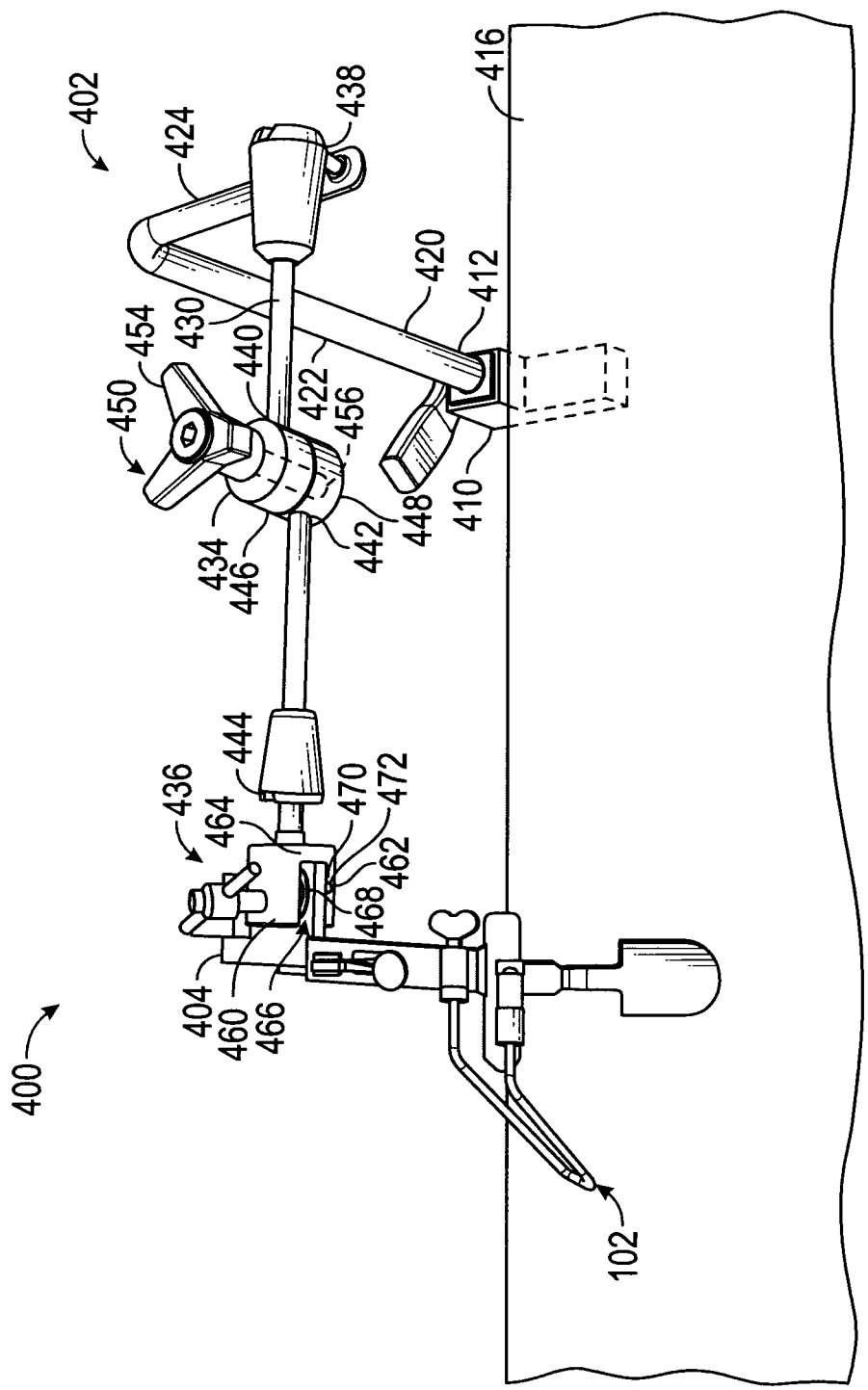
FIG. 26 is a perspective view of yet another embodiment of a surgical retractor system according to the inventive concepts disclosed herein.
Figure 27:
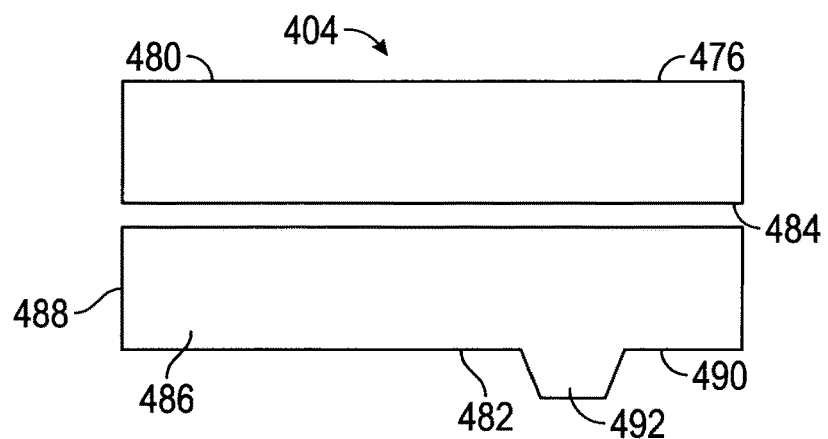
FIG. 27 is a front elevational view of an exemplary support bracket of the surgical system of FIG. 26.
Figure 28:
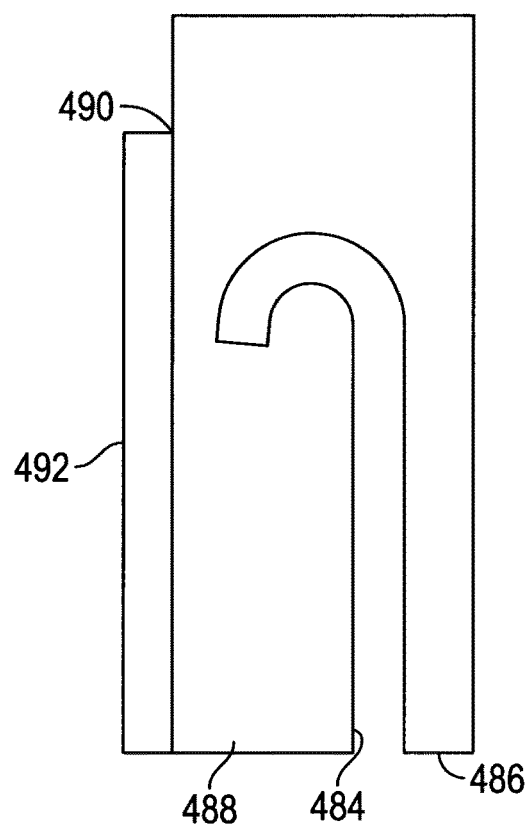
FIG. 28 is a side elevational view of the support bracket of FIG. 27.

Referring now to FIGS. 26-28, another example of a surgical retractor system 400 according to the inventive concepts disclosed herein is shown. The surgical retractor system 400 may be provided with a support brace assembly 402, a support bracket 404, and the surgical retractor 102. In general, the support brace assembly 402 may be provided with a table clamp 410, a vertical support assembly 412, and a horizontal support assembly 414. The table clamp 410 connects the vertical support assembly 412 to a supporting member 416, such as a surgical table. The vertical support assembly 412 is connected to the horizontal support assembly 414 and serves to rigidly support the horizontal support assembly 414 above the supporting member 416. The horizontal support assembly 414 is connected to and supports the support bracket 404, and the support bracket 404 is connected to and supports the surgical retractor 102.

In this example, the vertical support assembly 412 includes an L-shaped member 420, which is connected to and extends vertically from the table clamp 410. More particularly, the L-shaped member 420 is provided with a first leg 422 and a second leg 424. The first leg 422 is connected to the table clamp 410 and the second leg 424 is connected to the horizontal support assembly 414. As shown, the first leg 422 may extend generally normal from the second leg 424, although it should be understood that the first leg 422 may extend at other angles relative to the second leg 424.

In general, the horizontal support assembly 414 may be designed to articulate so as to provide lateral adjustment of the surgical retractor 102 relative to the supporting member 416. In the example shown, the horizontal support assembly 414 is provided with a first supporting member 430, a second supporting member 432, an adjustment mechanism 434, and a clamping mechanism 436. The first supporting member 430 is provided with a first end 438 and a second end 440. The first end 438 of the first supporting member 430 is connected to the second leg 424 of the L-shaped member 420. The second end 440 of the first supporting member 430 is connected to the adjustment mechanism 434. The second supporting member 432 is also provided with a first end 442, and a second end 444. The first end 442 of the second supporting member 432 is connected to the adjustment mechanism 434 and the second end 444 of the second supporting member 432 is connected to the clamping mechanism 436.

The adjustment mechanism 434 may be provided with a first member 446, a second member 448, and a biasing system 450. In this example, the first member 446 is connected to the second end 440, and the second member 448 is connected to the first end 442. The first member 446 may be movable relative to the second member 448 depending upon a setting of the biasing system 450. More particularly, in a first setting of the biasing system 450 the first member 446 may be freely movable relative to the second member 448, while in a second setting of the biasing system 450 the first member 446 may be locked, i.e., non-movable, relative to the second member 448. In one embodiment, the biasing system 450 includes a handle 454 connected to a threaded mechanism 456. The threaded mechanism 456 is positioned within a smooth bore (not shown) of the first member 446, and a threaded bore (not shown) of the second member 448. Upon rotation of the handle 454, the threaded mechanism 456 rotates and moves the second member 448 relative to the first member 446 to selectively clamp the first member 446 between the second member 448 and the handle 454 to either lock or unlock the first member 446 relative to the second member 448.

The clamping mechanism 436 may be provided with a first leg 460, a second leg 462, and a connecting member 464 connected to and supporting the first leg 460 and the second leg 462 in a spaced apart relationship so as to define a slot 466 between the first leg 460 and the second leg 462. The slot 466 may be sized and adapted to receive the support bracket 404. The clamping mechanism 436 is also provided with a clamping member 468 which is adjustably supported by the first leg 460 and extends towards the second leg 462. The clamping member 468 can be constructed in a variety of manners, such as a threaded rod with a handle connected to the threaded rod and positioned within a threaded bore extending through the first leg 460. The second leg 462 may be provided with an upper surface 470 having a notch 472 extending generally away from an outer boundary of the upper surface 470 into the second leg 462.

The support bracket 404 has a body 476. The clamping mechanism 436 connects to the body 476 by insertion of the body 476 into the slot 466, and clamping of the body 476 between the clamping member 468 and the second leg 462. In one embodiment, the body 476 is provided with a first end 480, a second end 482, and a slot 484 extending through a lower portion 486 and intersecting a first side 488. The slot 484 may be designed such that the end of the tongue blade 104 of the surgical retractor 102 may be slidably inserted into the support bracket 404 and secured therein via a thumbscrew or other type of securing mechanism. The second end 482 of the body 476 may be positioned on the second leg 462 and may also be adapted to mate with the upper surface 470 and the notch 472 of the second leg 462. For example, the second end 482 may be provided with a first surface 490 and a male member 492 extending from the first surface 490. When the body 476 is positioned within the slot 466, the male member 492 may be positioned within the notch 472 to prevent lateral movement of the second end 482 of the body 476 relative to the second leg 462.

In operation, an exemplary method for using the surgical retractor system 100 according to the inventive concepts disclosed herein may be implemented as follows. A surgeon may select an appropriately sized surgical retractor 102 for the respective patient or procedure. The surgeon may further select an appropriate tongue blade 104 depending on the particular procedure, patient, surgeon preferences, and combinations thereof. The selected tongue blade 104 may be a one-piece tongue blade, or a two-piece tongue blade, and may comprise an adjustable tip. The selected tongue blade 104 may comprise a holder adapted to hold the pin 218 in some embodiments. The surgeon may select more than one tongue blade 104 to be changed during different stages of the surgical procedure for example. The selected tongue blade 104 may be inserted into the handle 106 of the surgical retractor 102.

In any event, the surgical retractor 102 may be deployed or inserted into the patient's oral cavity by unlocking the lockable hinge 126, positioning the handle 106 and the bar 118 at an acute angle relative to one another, and inserting the surgical retractor 102 inside the oral cavity, such that the maxillary brace 134 is positioned against the patient's maxilla, and the tongue blade 104 is positioned against the patient's tongue. The tongue blade 104 may be adjusted by sliding the tongue blade 104 inside the holder 108 and securing the tongue blade 104 via the locking mechanism 110. The maxillary brace 134 may be adjusted by being rotated or pivoted about the second leg 122, for example. If the tongue blade 104 has an adjustable tip, the adjustable tip may likewise be adjusted as needed. Further, an appropriate tip may likewise be selected for use with the tongue blade 104, for example.

The handle 106 may be operated to increase the angle between the bar 118 and the handle 106, thus applying pressure to the patient's maxilla and tongue, which will tend to retract the patient's oral tissues. Once the desired retraction is achieved, the surgical retractor 102 may be locked in position via the operation of the lockable hinge 126.

In implementations where extra support is required, the surgical retractor 102 may be supported on a support surface such as the patent or a surgical table via a support brace 302 and a support bracket 300, for example. The angle between the support brace 302 and the support bracket 300 may be adjusted as desired.

If an emergency situation arises during the procedure, the surgeon may quickly and easily remove the surgical retractor 102 from the patient's oral cavity, by unlocking the lockable hinge 126, folding the surgical retractor 102, and sliding it out of the patient's oral cavity, for example.

In some versions, the presently disclosed inventive concepts describe a surgical retractor, comprising: a handle defining a tongue blade receiving opening, the handle having a locking mechanism adapted to selectively lock the tongue blade in position and defining a first plane; a bar having a first leg and a second leg, the first leg and the second leg cooperating to define a second plane; a locking hinge adapted to be locked at more than one surgical position; a tongue blade comprising a stem adapted to be slidable inserted into the handle, and a tip adapted to press against a tongue of a patient when the surgical retractor is inserted into an oral cavity of the patient; and wherein the handle and the bar may be moved relative to one another via the locking hinge such that the first plane and the second plane form an angle between about 0 degrees and about 360 degrees.

The locking hinge may further comprise a meshing gear member, a toothed shaft, and a thumb screw adapted to selectively lock the meshing gear member with the toothed shaft, the locking hinge hingedly connecting the first leg of the bar to the handle. The surgical retractor may further comprise one or more maxillary brace connected to the second leg, the one or more maxillary brace adapted to engage a patient's maxilla. In some versions, the second leg has an end having a first shape, and wherein the maxillary brace has an attachment portion having a second shape corresponding to the first shape, the attachment portion of the maxillary brace being configured to slide onto the end of the second leg in two or more positions and be locked in the two or more positions. The first shape of the end of the second leg may be selected from a group consisting of hexagonal, square octagonal, hex key, double hex key, pentalobular, and triangular shapes. In these versions, the locking hinge may be adapted to establish rotary movement between the handle and the bar.

In some versions, the presently disclosed inventive concepts describe a surgical retractor, comprising: a handle defining a tongue blade receiving opening, the handle having a locking mechanism adapted to selectively lock the tongue blade in position and defining a first plane; a bar having a first leg and a second leg, the first leg and the second leg cooperating to define a second plane, the second leg comprising an end having a first shape; one or more maxillary brace connected to the second leg, the one or more maxillary brace adapted to engage a patient's maxilla, and comprising an attachment portion having a second shape corresponding to the first shape of the end of the second leg, the attachment portion of the maxillary brace being configured to slide onto the end of the second leg in two or more positions and be locked in the two or more positions; a tongue blade comprising a stem adapted to be slidable inserted into the handle, and a tip adapted to press against a tongue of a patient when the surgical retractor is inserted into an oral cavity of the patient.

In some versions, the first shape of the end of the second leg is selected from a group consisting of hexagonal, square octagonal, hex key, double hex key, pentalobular, and triangular shapes.

In some versions, the presently disclosed inventive concepts describe a maxillary brace for a surgical retractor, the maxillary brace comprising: an attachment portion adapted to be connected to the surgical retractor; and a body attached to the attachment portion and comprising an engagement surface adapted to engage a patient's maxilla, the engagement surface comprising one or more of: one or more bumps, one or more striations, one or more grooves, one or more soft palate-engaging spikes, and one or more knurls. The attachment portion of the maxillary brace may be adapted to be rotatably connectable to the surgical retractor and further comprising a locking mechanism adjacent to the attachment portion for locking a position of the attachment portion relative to the surgical retractor.

In some versions, the presently disclosed inventive concepts describe a maxillary brace adapted to be connected to a surgical retractor, the maxillary brace comprising a body defining an engagement surface adapted to engage a patient's maxilla, the engagement surface comprising one or more spikes adapted to engage a soft palate tissue of a patient, such that the maxillary brace is at least partially securable to the patient's maxilla via the one or more spikes.

In some versions, the presently disclosed inventive concepts describe a multiple piece tongue blade comprising: a stem adapted to be inserted into a handle of a surgical retractor; a tip adapted to be selectively attached to the stem; and wherein the tip is insertable into a mouth of a patient such that the tip applies pressure onto a tongue of the patient.

In some versions, the presently disclosed inventive concepts describe a tongue blade, comprising: a stem adapted to be inserted into a handle of a surgical retractor; a tip attached to the stem, the tip having a first side, a second side, and at least one holder; and a pin connected to the holder and extending beyond the first side and the second side of the tip.

In some versions, the presently disclosed inventive concepts describe a tongue blade for a surgical retractor, comprising: a stem adapted to be inserted into a handle of a surgical retractor, the stem being substantially curved along a length of the stem; a tip connected to the stem; and wherein the tip is insertable into a mouth of a patient such that the tip applies pressure onto a tongue of the patient.

In some versions, the presently disclosed inventive concepts describe a support bracket for a surgical retractor system, the support bracket comprising: a body having an upper end, a lower end and a first side extending between the upper end and the lower end, the body defining a slot extending through the lower end and intersecting the first side, the slot shaped to receive a stem of a tongue blade for a surgical retractor; and a member supported by the body and being movable within the slot. The slot may have a first portion having an arc shape, and a second portion having a linear shape, and wherein the first portion is positioned between the second portion and the upper end of the body.

In some versions, the presently disclosed inventive concepts describe a multiple piece tongue blade comprising a stem adapted to be inserted into a handle of a surgical retractor, the stem having a teeth receiving section adapted to negotiate around mandibular teeth of a patient; a tip adapted to be selectively attached to the stem; and wherein the tip is insertable into a mouth of the patient such that the tip applies pressure onto a tongue of the patient.

The multiple piece tongue blade may further comprise at least one layer of padding covering at least a portion of the teeth receiving section. In one embodiment, the at least one layer of padding is formed of silastic. In some embodiments, the teeth receiving section is a U-shaped groove adapted to negotiate around mandibular teeth of a patient.

In some versions, the presently disclosed inventive concepts describe a tongue blade for a surgical retractor, comprising: a stem adapted to be inserted into a handle of a surgical retractor, the stem being substantially curved along a length of the stem and having a teeth receiving section adapted to negotiate around mandibular teeth of a patient; a tip supported by the stem; and wherein the tip is insertable into a mouth of the patient such that the tip applies pressure onto a tongue of the patient.

The tongue blade may further comprise at least one layer of padding positioned on the teeth receiving section. The at least one layer of padding may be formed of silastic. In some embodiments, the teeth receiving section has a U-shape with an opening positioned to receive at least a portion of a patient's mandibular teeth when the tip is inserted into the mouth of the patient. In some embodiments, the stem has a proximal portion adapted to be inserted into the handle of the surgical retractor, and wherein the opening faces the proximal portion.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the inventive concepts disclosed herein unless explicitly described as such outside of the preferred embodiment.

From the above description, it is clear that the inventive concepts disclosed herein are adapted to carry out the objects and to attain the advantages mentioned herein as well as those inherent in the inventive concepts disclosed herein. While presently preferred embodiments of the inventive concepts disclosed herein have been described for purposes of this disclosure, it will be understood that numerous changes may be made which will readily suggest themselves to those skilled in the art and which are accomplished within the scope of the inventive concepts disclosed herein and defined by the appended claims.

What is claimed is:

1. A surgical retractor, comprising:
   a handle defining a tongue blade receiving opening, the handle having a locking mechanism attached to a surface of the handle, the handle defining a first plane;
   a U-shaped bar comprising a first leg having a first free end, a second leg having a second free end, and a medial portion between the first leg and the second leg, the first leg and the second leg cooperating to define a second plane;
   a lockable hinge secured to the surface of the handle, and having at least two meshing elements adapted to be locked together at more than one surgical position, and the lockable hinge hingedly connecting only the first leg of the U-shaped bar to the handle, wherein the first free end of the first leg is inserted into the lockable hinge;
   a tongue blade comprising a stem and a tip, the stem of the tongue blade adapted to be slidably received into the tongue blade receiving opening of the handle, and the tip adapted to press against a tongue of a patient when the surgical retractor is inserted into an oral cavity of the patient, wherein the locking mechanism is adapted to selectively lock the tongue blade in position;
   one or more maxillary braces connected to the second leg of the U-shaped bar, the one or more maxillary braces adapted to engage a patient's maxilla;
   and
   wherein the handle and the U-shaped bar may be moved relative to one another via the lockable hinge such that the first plane and the second plane form an angle varying from about 0 degrees to about 180 degrees, and wherein the meshing elements of the lockable hinge are adjustable relative to one another and securely locked together at any desired angle from about 0 degrees to about 180 degrees.

2. The surgical retractor of claim 1, wherein one of the meshing elements of the lockable hinge is a meshing gear member, and another one of the meshing elements is a toothed shaft, and wherein the lockable hinge further comprises a thumb screw adapted to selectively lock the meshing gear member with the toothed shaft.

3. The surgical retractor of claim 1, wherein the one or more maxillary braces are rotatably connected to the second leg of the U-shaped bar.

4. The surgical retractor of claim 1, wherein the second free end of the second leg has a first shape, and wherein the one or more maxillary braces have an attachment portion having a second shape corresponding to the first shape, the attachment portion of each maxillary brace being configured to slide onto the second free end of the second leg in two or more positions and be locked in the two or more positions.

5. The surgical retractor of claim 4, wherein the first shape of the second free end of the second leg is selected from a group consisting of hexagonal, square, octagonal, hex key, double hex key, pentalobular, and triangular shapes.

6. A surgical retractor, comprising:
   a handle defining a tongue blade receiving opening, the handle having a locking mechanism attached to a surface of the handle, the handle defining a first plane;
   a bar comprising a first leg having a first free end, a second leg having a second free end, and a medial portion between the first leg and the second leg, the first leg and the second leg cooperating to define a second plane;
   a lockable hinge secured to the surface of the handle, and adapted to be locked at more than one surgical position, and the lockable hinge hingedly connecting the first free end of the first leg of the bar to the handle, wherein the first free end of the first leg is inserted into the lockable hinge, and, wherein the lockable hinge comprises a meshing gear member, a toothed shaft, and a thumb screw adapted to selectively lock the meshing gear member with the toothed shaft;
   a tongue blade comprising a stem and a tip, the stem of the tongue blade adapted to be slidably received into the tongue blade receiving opening of the handle, and the tip adapted to press against a tongue of a patient when the surgical retractor is inserted into an oral cavity of the patient, wherein the locking mechanism is adapted to selectively lock the tongue blade in position;
   one or more maxillary braces connected to the second leg of the bar, the one or more maxillary braces adapted to engage a patient's maxilla;
   and
   wherein the handle and the bar may be moved relative to one another via the lockable hinge such that the first plane and the second plane form an angle varying from about 0 degrees to about 180 degrees, and wherein the lockable hinge is adjustable and securely locked together at any desired angle from about 0 degrees to about 180 degrees.

7. The surgical retractor of claim 6, wherein the one or more maxillary braces are rotatably connected to the second leg of the bar.

8. The surgical retractor of claim 6, wherein the second free end of the second leg has a first shape, and wherein the one or more maxillary braces have an attachment portion having a second shape corresponding to the first shape, the attachment portion of each maxillary brace being configured to slide onto the second free end of the second leg in two or more positions and be locked in the two or more positions.

9. The surgical retractor of claim 8, wherein the first shape of the second free end of the second leg is selected from a group consisting of hexagonal, square, octagonal, hex key, double hex key, pentalobular, and triangular shapes.

* * * * *